(12) United States Patent
Masuda et al.

(10) Patent No.: US 11,684,909 B2
(45) Date of Patent: *Jun. 27, 2023

(54) STRUCTURED CATALYST FOR METHANOL REFORMING, METHANOL REFORMING DEVICE, METHOD FOR PRODUCING STRUCTURED CATALYST FOR METHANOL REFORMING, AND METHOD FOR PRODUCING AT LEAST ONE OF OLEFIN OR AROMATIC HYDROCARBON

(71) Applicant: FURUKAWA ELECTRIC CO., LTD., Tokyo (JP)

(72) Inventors: Takao Masuda, Sapporo (JP); Yuta Nakasaka, Sapporo (JP); Takuya Yoshikawa, Sapporo (JP); Sadahiro Kato, Tokyo (JP); Masayuki Fukushima, Tokyo (JP); Hiroko Takahashi, Tokyo (JP); Yuichiro Banba, Tokyo (JP); Kaori Sekine, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/698,527

(22) Filed: Nov. 27, 2019

(65) Prior Publication Data

US 2020/0114335 A1 Apr. 16, 2020

Related U.S. Application Data

(63) Continuation of application No. PCT/JP2018/021094, filed on May 31, 2018.

(30) Foreign Application Priority Data

May 31, 2017 (JP) ................................ 2017-108613

(51) Int. Cl.
*B01J 29/06* (2006.01)
*B01J 29/04* (2006.01)
(Continued)

(52) U.S. Cl.
CPC ............ *B01J 29/041* (2013.01); *B01J 23/06* (2013.01); *B01J 23/10* (2013.01); *B01J 23/16* (2013.01);
(Continued)

(58) Field of Classification Search
CPC .. B01J 29/035; B01J 29/0308; B01J 29/0352; B01J 29/0354; B01J 29/0356; B01J 29/0358; B01J 29/041; B01J 29/044; B01J 29/043; B01J 29/064; B01J 29/068; B01J 29/072; B01J 29/076; B01J 29/085; B01J 29/10; B01J 29/12; B01J 29/14; B01J 29/16; B01J 29/185; B01J 29/20; B01J 29/22; B01J 29/24; B01J 29/26; B01J 29/42; B01J 29/44; B01J 29/46; B01J 29/48; B01J 29/405; B01J 29/605; B01J 29/61; B01J 29/62; B01J 29/63; B01J 29/64; B01J 29/655; B01J 29/66; B01J 29/67; B01J 29/68; B01J 29/69; B01J 29/7007; B01J 29/7057; B01J 29/7038; B01J 29/7088; B01J 29/7615; B01J 29/7676; B01J 29/7815; B01J 29/7876; B01J 29/7415; B01J 29/7215; B01J 29/7476; B01J 29/7276; B01J 2229/22; B01J 2229/40; B01J 2229/38; B01J 2229/126; B01J 2229/20; B01J 2229/32; B01J 2229/34; B01J 35/006; B01J 35/0066; B01J 35/026; B01J 35/023; B01J 35/0073; B01J 35/0046; B01J 37/0018; B01J 37/0072; B01J 37/0201; B01J 37/0207; B01J 37/0203; B01J 37/0205; B01J 37/10; B01J 37/08; B01J 37/105; B01J 35/1057; B01J 35/1061; B01J 29/40; B01J 29/65; B01J 29/70; B01J 23/06; B01J 23/10;
(Continued)

(56) References Cited

U.S. PATENT DOCUMENTS 3,898,180 A 8/1975 Crooks et al.
4,552,855 A 11/1985 Ozin et al.
(Continued)

FOREIGN PATENT DOCUMENTS

AU 2012324802 A1 6/2014
CA 2256515 A1 12/1997
(Continued)

OTHER PUBLICATIONS

Machine translation CN 102247887, Nov. 2011.*
(Continued)

*Primary Examiner* — Elizabeth D Wood
(74) *Attorney, Agent, or Firm* — Dorsey & Whitney LLP

(57) ABSTRACT

To provide a highly active structured catalyst for methanol reforming that suppresses the decline in catalytic function and has excellent catalytic function, and a methanol reforming device. A structured catalyst for methanol reforming, including:

a support of a porous structure composed of a zeolite-type compound; and a catalytic substance present in the support, in which the support has channels communicating with each other, and the catalytic substance is present at least in the channels of the support.

13 Claims, 4 Drawing Sheets

(51) Int. Cl.
| | |
|---|---|
| *B01J 35/02* | (2006.01) |
| *B01J 35/10* | (2006.01) |
| *B01J 37/02* | (2006.01) |
| *B01J 37/08* | (2006.01) |
| *B01J 29/035* | (2006.01) |
| *B01J 29/03* | (2006.01) |
| *B01J 29/072* | (2006.01) |
| *B01J 29/08* | (2006.01) |
| *B01J 29/14* | (2006.01) |
| *B01J 29/12* | (2006.01) |
| *B01J 29/10* | (2006.01) |
| *B01J 29/064* | (2006.01) |
| *B01J 29/076* | (2006.01) |
| *B01J 29/42* | (2006.01) |
| *B01J 29/20* | (2006.01) |
| *B01J 29/44* | (2006.01) |
| *B01J 29/24* | (2006.01) |
| *B01J 29/16* | (2006.01) |
| *B01J 29/22* | (2006.01) |
| *B01J 29/26* | (2006.01) |
| *B01J 29/18* | (2006.01) |
| *B01J 29/62* | (2006.01) |
| *B01J 29/65* | (2006.01) |
| *B01J 29/48* | (2006.01) |
| *B01J 29/40* | (2006.01) |
| *B01J 29/64* | (2006.01) |
| *B01J 29/46* | (2006.01) |
| *B01J 29/60* | (2006.01) |
| *B01J 29/61* | (2006.01) |
| *B01J 29/63* | (2006.01) |
| *B01J 29/70* | (2006.01) |
| *B01J 29/66* | (2006.01) |
| *B01J 29/67* | (2006.01) |
| *B01J 29/69* | (2006.01) |
| *B01J 29/68* | (2006.01) |
| *B01J 29/76* | (2006.01) |
| *B01J 29/72* | (2006.01) |
| *B01J 29/74* | (2006.01) |
| *B01J 29/78* | (2006.01) |
| *B01J 23/32* | (2006.01) |
| *B01J 23/36* | (2006.01) |
| *B01J 23/06* | (2006.01) |
| *B01J 23/34* | (2006.01) |
| *B01J 23/10* | (2006.01) |
| *B01J 23/16* | (2006.01) |
| *B01J 23/745* | (2006.01) |

(52) U.S. Cl.
CPC .............. *B01J 23/32* (2013.01); *B01J 23/34* (2013.01); *B01J 23/36* (2013.01); *B01J 23/745* (2013.01); *B01J 29/035* (2013.01); *B01J 29/0308* (2013.01); *B01J 29/0352* (2013.01); *B01J 29/0354* (2013.01); *B01J 29/0356* (2013.01); *B01J 29/0358* (2013.01); *B01J 29/043* (2013.01); *B01J 29/044* (2013.01); *B01J 29/064* (2013.01); *B01J 29/072* (2013.01); *B01J 29/076* (2013.01); *B01J 29/085* (2013.01); *B01J 29/10* (2013.01); *B01J 29/12* (2013.01); *B01J 29/14* (2013.01); *B01J 29/16* (2013.01); *B01J 29/185* (2013.01); *B01J 29/20* (2013.01); *B01J 29/22* (2013.01); *B01J 29/24* (2013.01); *B01J 29/26* (2013.01); *B01J 29/405* (2013.01); *B01J 29/42* (2013.01); *B01J 29/44* (2013.01); *B01J 29/46* (2013.01); *B01J 29/48* (2013.01); *B01J 29/605* (2013.01); *B01J 29/61* (2013.01); *B01J 29/62* (2013.01); *B01J 29/63* (2013.01); *B01J 29/64* (2013.01); *B01J 29/65* (2013.01); *B01J 29/655* (2013.01); *B01J 29/66* (2013.01); *B01J 29/67* (2013.01); *B01J 29/68* (2013.01); *B01J 29/69* (2013.01); *B01J 29/70* (2013.01); *B01J 29/7007* (2013.01); *B01J 29/7038* (2013.01); *B01J 29/7057* (2013.01); *B01J 29/7088* (2013.01); *B01J 29/7215* (2013.01); *B01J 29/7276* (2013.01); *B01J 29/7415* (2013.01); *B01J 29/7476* (2013.01); *B01J 29/7676* (2013.01); *B01J 29/7815* (2013.01); *B01J 29/7876* (2013.01); *B01J 35/023* (2013.01); *B01J 35/1057* (2013.01); *B01J 37/0207* (2013.01); *B01J 37/08* (2013.01); *B01J 2229/126* (2013.01); *B01J 2229/20* (2013.01); *B01J 2229/22* (2013.01); *B01J 2229/32* (2013.01); *B01J 2229/34* (2013.01); *B01J 2229/38* (2013.01); *B01J 2229/40* (2013.01)

(58) Field of Classification Search
CPC ... B01J 23/16; B01J 23/32; B01J 23/34; B01J 23/36; B01J 23/745; C10G 2300/70; C01B 39/02; Y02P 30/20; Y02P 30/40
USPC ........ 502/60, 63, 64, 65, 66, 69, 71, 73, 74, 502/77, 78, 79
See application file for complete search history.

(56) References Cited

U.S. PATENT DOCUMENTS

| | | | |
|---|---|---|---|
| 5,026,673 A | 6/1991 | Gates et al. | |
| 5,236,575 A | 8/1993 | Bennett et al. | |
| 5,275,720 A | 1/1994 | Ward | |
| 5,849,652 A | 12/1998 | Davies et al. | |
| 5,994,603 A | 11/1999 | Mohr et al. | |
| 6,040,259 A | 3/2000 | Mohr et al. | |
| 6,831,203 B1 | 12/2004 | Mohr et al. | |
| 6,881,703 B2 | 4/2005 | Cutler et al. | |
| 7,074,373 B1 | 7/2006 | Warren et al. | |
| 7,592,291 B2 | 9/2009 | Rollins et al. | |
| 7,893,311 B2 | 2/2011 | Takamatsu et al. | |
| 11,161,101 B2 * | 11/2021 | Kato | B01J 23/464 |
| 2003/0109383 A1 | 6/2003 | Koike et al. | |
| 2003/0188991 A1 | 10/2003 | Shan et al. | |
| 2004/0176245 A1 | 9/2004 | Hagemeyer et al. | |
| 2004/0192947 A1 | 9/2004 | Chane-ching et al. | |
| 2005/0201920 A1 | 9/2005 | Shan et al. | |
| 2006/0211777 A1 | 9/2006 | Severinsky | |
| 2006/0216227 A1 | 9/2006 | Idem et al. | |
| 2007/0004593 A1 | 1/2007 | Ohno et al. | |
| 2007/0167551 A1 | 7/2007 | Goodwin et al. | |
| 2008/0045400 A1 | 2/2008 | Rollins et al. | |
| 2008/0045403 A1 | 2/2008 | Rollins et al. | |
| 2008/0051280 A1 | 2/2008 | Hagemeyer et al. | |
| 2008/0072705 A1 | 3/2008 | Chaumonnot et al. | |
| 2008/0280754 A1 | 11/2008 | Toledo et al. | |
| 2008/0293990 A1 | 11/2008 | Stevenson et al. | |
| 2009/0286677 A1 | 11/2009 | Takeshima et al. | |
| 2009/0325790 A1 | 12/2009 | Haller et al. | |
| 2010/0004118 A1 | 1/2010 | Liu et al. | |
| 2011/0085944 A1 | 4/2011 | Rolllins et al. | |
| 2011/0092356 A1 | 4/2011 | Rollins et al. | |
| 2011/0092745 A1 | 4/2011 | Senoo et al. | |
| 2011/0121238 A1 | 5/2011 | Wakatsuki | |
| 2011/0293941 A1 | 12/2011 | Chaumonnot et al. | |
| 2012/0042631 A1 | 2/2012 | Schmieg et al. | |
| 2012/0060472 A1 | 3/2012 | Li et al. | |
| 2012/0130138 A1 | 5/2012 | Yamaguchi et al. | |
| 2012/0142238 A1 | 6/2012 | Saitou et al. | |
| 2012/0231948 A1 | 9/2012 | Saito | |
| 2013/0041174 A1 | 2/2013 | Yamamoto et al. | |

(56) References Cited

U.S. PATENT DOCUMENTS

| | | |
|---|---|---|
| 2013/0090445 A1 | 4/2013 | Hattori et al. |
| 2014/0021096 A1 | 1/2014 | Chaumonnot et al. |
| 2014/0128246 A1 | 5/2014 | Garcia-martinez |
| 2014/0147362 A1 | 5/2014 | Sasaki et al. |
| 2014/0284524 A1 | 9/2014 | Lee et al. |
| 2014/0303266 A1* | 10/2014 | Hyman ............... B01J 29/146 502/79 |
| 2015/0018590 A1 | 1/2015 | Stevenson et al. |
| 2015/0290635 A1 | 10/2015 | Inokawa et al. |
| 2015/0367332 A1 | 12/2015 | Kuvettu et al. |
| 2016/0017238 A1 | 1/2016 | Stamires et al. |
| 2016/0023913 A1 | 1/2016 | Goel et al. |
| 2016/0024400 A1 | 1/2016 | Iwasa et al. |
| 2016/0030934 A1 | 2/2016 | Zhan et al. |
| 2016/0032202 A1 | 2/2016 | Yonemura et al. |
| 2016/0087285 A1 | 3/2016 | Watanabe et al. |
| 2016/0114314 A1 | 4/2016 | Ali et al. |
| 2016/0137516 A1 | 5/2016 | Kegnæs et al. |
| 2016/0369174 A1 | 12/2016 | Kool et al. |
| 2017/0036197 A1 | 2/2017 | Kegnæs et al. |
| 2018/0194700 A1 | 7/2018 | Pan et al. |
| 2019/0039056 A1 | 2/2019 | Kato et al. |
| 2020/0094229 A1 | 3/2020 | Masuda et al. |
| 2020/0094232 A1 | 3/2020 | Masuda et al. |
| 2020/0108374 A1 | 4/2020 | Masuda et al. |
| 2020/0108378 A1 | 4/2020 | Masuda et al. |
| 2020/0114336 A1 | 4/2020 | Masuda et al. |
| 2020/0114337 A1 | 4/2020 | Masuda et al. |
| 2020/0114338 A1 | 4/2020 | Masuda et al. |
| 2020/0114339 A1 | 4/2020 | Masuda et al. |
| 2020/0114341 A1 | 4/2020 | Masuda et al. |
| 2020/0115248 A1 | 4/2020 | Masuda et al. |
| 2020/0115640 A1 | 4/2020 | Masuda et al. |
| 2020/0254432 A1 | 8/2020 | Shirman et al. |

FOREIGN PATENT DOCUMENTS

| | | |
|---|---|---|
| CN | 1223602 A | 7/1999 |
| CN | 1720098 A | 1/2006 |
| CN | 1729138 A | 2/2006 |
| CN | 1876766 A | 12/2006 |
| CN | 101130466 A | 2/2008 |
| CN | 101180125 A | 5/2008 |
| CN | 101362959 A | 2/2009 |
| CN | 101720252 A | 6/2010 |
| CN | 101909750 A | 12/2010 |
| CN | 102056869 A | 5/2011 |
| CN | 102099114 A | 6/2011 |
| CN | 102247887 A | 11/2011 |
| CN | 102400744 A | 4/2012 |
| CN | 102574120 A | 7/2012 |
| CN | 102844115 A | 12/2012 |
| CN | 103459012 A | 12/2013 |
| CN | 103663490 A | 3/2014 |
| CN | 103889577 A | 6/2014 |
| CN | 104650291 A | 5/2015 |
| CN | 105008492 A | 10/2015 |
| CN | 105347359 A | 2/2016 |
| CN | 106362787 A | 2/2017 |
| EP | 0485180 A1 | 5/1992 |
| EP | 1709125 A1 | 10/2006 |
| EP | 2484444 A1 | 8/2012 |
| EP | 2692439 A1 | 2/2014 |
| EP | 2992984 A1 | 3/2016 |
| JP | S5746925 A | 3/1982 |
| JP | H0549943 * | 3/1993 |
| JP | H0549943 A | 3/1993 |
| JP | H06-142456 A | 5/1994 |
| JP | H07-096195 A | 4/1995 |
| JP | H08155303 A | 6/1996 |
| JP | H1133412 A | 2/1999 |
| JP | H11151440 A | 6/1999 |
| JP | 2000197822 A | 7/2000 |
| JP | 2000511107 A | 8/2000 |
| JP | 2000323164 A | 11/2000 |
| JP | 2002255537 A | 9/2002 |
| JP | 2002336704 A | 11/2002 |
| JP | 2004528158 A | 9/2004 |
| JP | 2005170903 A | 6/2005 |
| JP | 2005189586 A | 7/2005 |
| JP | 2005270734 A | 10/2005 |
| JP | 2005314208 A | 11/2005 |
| JP | 2006021994 A | 1/2006 |
| JP | 2007130525 A | 5/2007 |
| JP | 2007519799 A | 7/2007 |
| JP | 2008012382 A | 1/2008 |
| JP | 2008542177 A | 11/2008 |
| JP | 2009505830 A | 2/2009 |
| JP | 2009255014 A | 11/2009 |
| JP | 2010501496 A | 1/2010 |
| JP | 2010099638 A | 5/2010 |
| JP | 2010527769 A | 8/2010 |
| JP | 2011517439 A | 6/2011 |
| JP | 4879574 B2 | 2/2012 |
| JP | 2012153654 A | 8/2012 |
| JP | 2012170951 A | 9/2012 |
| JP | 2012210557 A | 11/2012 |
| JP | 2013255911 A | 12/2013 |
| JP | 2014104428 A | 6/2014 |
| JP | 2014534902 A | 12/2014 |
| JP | 5700376 B2 | 4/2015 |
| JP | 2015165138 A | 9/2015 |
| JP | 2015189586 A | 11/2015 |
| JP | 2016002527 A | 1/2016 |
| JP | 2016064407 A | 4/2016 |
| JP | 2016069318 A | 5/2016 |
| JP | 2016087522 A | 5/2016 |
| JP | 2016529190 A | 9/2016 |
| JP | 2017039218 A | 2/2017 |
| JP | 2017064647 A | 4/2017 |
| JP | 2017509732 A | 4/2017 |
| JP | 2017128480 A | 7/2017 |
| WO | 9745197 A1 | 12/1997 |
| WO | 9745387 A1 | 12/1997 |
| WO | 2005083014 A1 | 9/2005 |
| WO | 2007000847 A1 | 1/2007 |
| WO | 2007023558 A1 | 3/2007 |
| WO | 2009096548 A1 | 8/2009 |
| WO | 2010097108 A1 | 9/2010 |
| WO | 2010097224 A2 | 9/2010 |
| WO | 2011065194 A1 | 6/2011 |
| WO | 2012105581 A1 | 8/2012 |
| WO | 2012170421 A1 | 12/2012 |
| WO | 2013057319 A2 | 4/2013 |
| WO | 2013115213 A1 | 8/2013 |
| WO | 2014083772 A1 | 6/2014 |
| WO | 2014132367 A1 | 9/2014 |
| WO | 2015001123 A1 | 1/2015 |
| WO | 2015155216 A1 | 10/2015 |
| WO | 2016014691 A1 | 1/2016 |
| WO | 2016181622 A1 | 11/2016 |
| WO | 2017000427 A1 | 1/2017 |
| WO | 2017072698 A1 | 5/2017 |

OTHER PUBLICATIONS

Do et al., "Zeolite Nanoclusters Coated onto the Mesopore Walls of SBA-15", J. Am. Chem. Soc. 2004, 126, pp. 14324-14325.*
English translation of International Preliminary Report on Patentability for Application No. PCT/JP2018/021094, dated Dec. 3, 2019.
English translation of Written Opinion for Application No. PCT/JP2018/021094, dated Aug. 21, 2018.
International Search Report (EN translation of ISR only) and Written Opinion for Application No. PCT/JP2018/021094, dated Aug. 21, 2018.
Fujikawa, Takashi, "Current Status and Future Prospects of Petroleum Refining Catalysts", The Nikkan Kogyo Shimbun, Ltd., vol. 65, No. 1, Jan. 1, 2017, p. 22.
Fumoto, Eri et al., "Catalytic Cracking of Heavy Oil With Iron Oxide-Based Catalysts Using Hydrogen and Oxygen Species From

(56) References Cited

OTHER PUBLICATIONS

Steam", Journal of the Japan Petroleum Institute, vol. 58, No. 5, Feb. 25, 2015, 329-335.
Haruta, Masatake, "Low-Temperature Combustion Catalysts Mainly for CO Oxidation", Journal of the Japan Petroleum Institute, vol. 37, No. 5, Sep. 1, 1994, pp. 480-491.
Ichikawa, Masaru et al., "Advanced Technology of Methane Chemical Conversion", CMC Publishing Co., Ltd., Jan. 2008.
Ismagilov, Z.R. et al., "Structural Changes of MO/ZSM-5 Catalysts During the Ethane Dehydroaromatization", Eurasian Chemico-Technological Journal, Journal 12, Nov. 2009, 9-16.
Laprune, David et al., "Highly Dispersed Nickel Particles Encapsulated in Multi-Hollow Silicalite-1 Single Crystal Nanoboxes: Effects of Siliceous Deposits and Phosphorous Species on the Catalytic Performances", ChemCatChem, vol. 9, Issue 12, dated Feb. 18, 2017, pp. 2297-2307.
Muroi, Takajyo, "Development Trends of Methane Chemistry Catalysts", Catalyst Round-table Conference News, No. 96, Nov. 1, 2016.
Muroi, Takashiro, "Reverse Water Gas Shift Catalysts", Industrial Catalyst News, No. 107, Aug. 1, 2017, 2 pages.
Sasaki, Makoto et al., "Templating Fabrication of Platinum Nanoparticles and Nanowires Using the Confined Mesoporous Channels of FSM-16—Their Structural Characterization and Catalytic Performances in Water Gas Shift Reaction", Journal of Molecular Catalysis A: Chemical, vol. 141, No. 1/3, May 6, 1999, p. 223-240.
Wu, Zhijie et al., "Hydrothermal Synthesis of LTA-Encapsulated Metal Clusters and Consequences for Catalyst Stability, Reactivity, and Selectivity", Journal of Catalysis, vol. 311, dated Jan. 31, 2014, pp. 458-468.
English machine translation of JP 2000-511107 A, entitled "Metal-containing zeolite catalyst, its preparation and use for the conversion of hydrocarbons".
English machine translation of JPH0796195 A, entitled "Exhaust Gas Purification Catalyst" dated Sep. 29, 1993.
https://sites.engineering.ucsb.edu/~jbraw/chemreacfun/ch7/slides-masswrxn-2up.pdf, College of Engineering, UC Santa Barbara accessed Apr. 26, 2021.
Dai, Chengyi et al., "Hollow zeolite-encapsulated Fe—Cu bimetallic catalysts for phenol degradation", Catalysis Today, Elsevier, Amsterdam, NL, vol. 297, Feb. 7, 2017 (Feb. 7, 2017), pp. 335-343, XP085215768, ISSN: 0920-5861, DOI: 10.1016/J.CATTOD.2017.02.001.
Li, Shiwen et al., "Diffusion Driven Selectivity in Oxidation of CO in Presence of Propylene Using Zeolite NANO Shell as Membrane", ACS Catalysis, vol. 4, No. 12, Dec. 2014, pp. 4299-4303.
Li, Shiwen et al., "Diffusion-Driven Selectivity in Oxidation of CO in the Presence of Propylene Using Zeolite NANO Shell as Membrane", ACS Catalysis, vol. 4, No. 12, Nov. 2014.
English machine translation of CN 106362787 A, entitled "Preparation method for zeolite-immobilized photocatalyst" dated Feb. 1, 2017.
English machine translation of JP 2002255537 A entitled "Solid Acid Catalyst" dated Sep. 11, 2002.
English machine translation of JP 2005314208 A entitled "Combined Porous Body and Its Manufacturing Method and Organic Substance Converting Method Using the Same" dated Nov. 10, 2005.
English machine translation of JP 2012170951 A entitled "Photocatalyst-Adsorbent Composite Powder" dated Sep. 10, 2012.
English machine translation of JP 2015165138 A entitled "Exhaust Gas Emission Control Device" dated Sep. 17, 2015.
English machine translation of JP 2016069318 A entitled "Storing Method for Secondary Alcohol and Loaded Body" dated May 9, 2016.
English machine translation of JP 2017128480 A entitled "Zeolite Including Metal Particle" dated Jul. 27, 2017.
English machine translation of JP H0549943A entitled "Oxidizing Catalyst" dated Mar. 2, 1993.
English machine translation of JPH1133412 entitled "A Production of Metal-Supporting Catalyst" dated Feb. 9, 1999.
English machine translation of WO 2007/023558 A1 entitled "Tungsten Oxide Photocatalyst, Process for Producing the Same, and Fiber Cloth Having Deodorizing/Antifouling Function" dated Mar. 1, 2007.
English machine translation of WO 2009/096548 A1 entitled "Silver-(Titanium Oxide)-Zeolite Adsorbent/Decomposing Material and Process for Production Thereof" dated Aug. 6, 2009.
English machine translation of WO 2012/105581 A1 entitled "Method for Producing Oxide Semiconductor Layer" dated Sep. 8, 2012.
Extended European Search Report received in EP App. No. 18808807.4 dated Dec. 7, 2020.
Dai, Chengyi et al., "Hollow Zeolite Encapsulated Ni—Pt Bimetals for Sintering and Coking Resistant Dry Reforming of Methane", Journal of Materials Chemistry A, vol. 3, No. 32, Jun. 29, 2015, pp. 16461-16468.
Liu, Xue et al., "Drying Of Ni/Alumina Catalysts: Control of the Metal Distribution Using Surfactants and the Melt Infiltration Methods", Industrial & Engineering Chemistry Research, vol. 53, No. 14, Apr. 9, 2014, pp. 5792-5800.
Makshina, Ekaterina et al., "Methanol Oxidation On LaCo Mixed Oxide Supported Onto MCM-41 Molecular Sieve", Catalysis Today, vol. 131, No. 1, Nov. 2007, pp. 427-430.
Maneesha, Mishra et al., "[alpha]-Fe2O3 as a photocatalytic material: A review", Applied Catalysis A: General, Elsevier, Amsterdam, NL, vol. 498, Mar. 28, 2015 (Mar. 28, 2015), pp. 126-141, XP029220089, ISSN: 0926-860X, DOI: 10.1016/J.APCATA.2015.03.023.
Wang, Hong et al., "Research into eliminating particulate from diesel engine exhaust over zeolite covered with catalysts of perovskite-type oxides", 2009 International Conference on Energy and Environment Technology : ICEET 2009 ; Guilin, China, Oct. 16-18, 2009, IEEE, Piscataway, NJ, USA, Oct. 16, 2009 (Oct. 16, 2009), pp. 493-495, XP031588294, ISBN: 978-0-7695-3819-8.
Yokoi, Toshiyuki, "Characterization of Zeolites by Advanced SEM/STEM Techniques", The Hitachi Scientific Instrument News, vol. 7, Sep. 2016, pp. 17-23.
Yue, Ming B. et al., "Directly Transforming AS-Synthesized MCM-41 to Mesoporous MFI Zeolite", Journal of Material Chemistry, vol. 18, No. 17, Mar. 13, 2008, p. 2044.
Zhijie, Wu et al., Hydrothermal synthesis of LTA-encapsulated metal clusters and consequences for catalyst stability, reactivity, and selectivity, Journal of Catalysis, Academic Press, Duluth, MN, US, vol. 311, Jan. 31, 2014 (Jan. 31, 2014), pp. 458-468, XP028612174, ISSN: 0021-9517, DOI: 10.1016/J.JCAT.2013.12.021.
English Translation of CN 102247887(A).
Wang, D Y. et al., Study on methane aromatization over MoO3/HMCM-49 catalyst, 2004, Catalysis Today, 93-95, Jul. 2, 2004, 75-80.
Cho, Hong J. et al., "Zeolite-Encapsualted Pt Nanoparticlles for Tandem Catalysis", J. Am. Chem. Soc., Sep. 24, 2018, 13514-13520.
Li, Peijun et al., "Ultrastable Perovskite-Zeolite Composite Enabled by Encapsulation and In Situ Passivation", Angewandte Chemie International Edition vol. 59, Issue 51, Sep. 5, 2020, 23300-23306.
Wang, Junwen et al., "In Situ Encapsulated Pt Nanoparticles Dispersed in Low Temperature Oxygen for Partial Oxidation of Methane to Syngas", Catalysts, Aug. 27, 2019, 720-734.
Newsam, J.M., "The Zeolite Cage Structure", Science, Mar. 7, 1986, New Series, vol. 231, No. 2742, pp. 1093-1099 (Year: 1986).
Wen, et al., "Enhanced catalytic performance of Co/MFI by hydrothermal treatment", Catalysis Letters vol. 86, Nos. 1-3, Mar. 2003.
[English Translation] Notice of Reasons for Refusal dated Feb. 7, 2022 for Japanese Patent Application No. 2019-521334; pp. all.
[English Translation] Notice of Reasons for Refusal dated Feb. 7, 2022 for Japanese Patent Application No. 2019-521335; pp. all.
[English Translation] Notice of Reasons for Refusal dated Feb. 7, 2022 for Japanese Patent Application No. JP2019-521325; pp. all.
[English Translation] Notice of Reasons for Refusal dated Mar. 16, 2022 for Japanese Patent Application No. 2019-521322; pp. all.

(56) References Cited

OTHER PUBLICATIONS

[English Translation] Notice of Reasons for Refusal dated Mar. 16, 2022 for Japanese Patent Application No. 2019-521331; pp. all.
[English Translation] Notice of Reasons for Refusal dated Mar. 28, 2022 for Japanese Patent Application No. 2019-521324; pp. all.
[English Translation] Saudi Arabian Office Action dated Jan. 27, 2022 for Saudi Arabian Patent Application No. 519410663; pp. all.
Cai et al. "Gold Nanoclusters Confined in a Supercage of Y Zeolite for Aerobic Oxidation of HMF under Mild Conditions", Chem. Rur. J, 2013, 19, pp. 14215-14223.
Corma et al. "A zeolite with interconnected 8-, 10-, and 12-ring pores and its unique catalytic selectivity", Nature Materials, vol. 2, Jun. 22, 2003, pp. 493-499.
Corma et al. "ITQ-15: The First ultralarge pore zeolite with a bi-directional pore system formed by intersecting 14- and 12-ring channels, and its catalytic implications", Chem. Commun., May 18, 2004, pp. 1356-1357.
Kalogeras et al. "Electrical Properties of Zeolitic Catalysts", Defect and Diffusion Forum vol. 164, Sep. 1998, pp. 1-36.
Mitra et al. "Molecular dynamics using quasielastic neutron scattering", Current Science, vol. 84, No. 5, Mar. 2003; pp. 653-662.
Nan Jiang et al. "The Adsorption Mechanisms of Organic Micropollutants on High-Silica Zeolites Causing S-Shaped Adsorption Isotherms: An Experimental and Monte Carlo Simulations Study", Chemical Engineering Journal; Nov. 2019; pp. all.
Do, Trong-On , et al., "Zeolite Nanoclusters Coated onto the Mesopore Walls of SBA-15", J. Am. Chem. SOC. vol. 126, No. 44, 2004, pp. 14324-14325.
[English Translation] First Office Action dated Jul. 5, 2022 for Chinese Patent Application No. 201880035017.7.
[English Translation] First Office Action dated Jun. 29, 2022 for Chinese Patent Application No. 201880036388.7.
[English Translation] First Office Action dated on Jun. 27, 2022 for Chinese Patent Application No. 201880035525.5.
Hosseinpour, Negahdar , et al., "Cumene cracking activity and enhanced regeneration of FCC catalystscomprising HY-zeolite and LaBO3(B = Co, Mn, and Fe) perovskites", Applied Catalysis A, vol. 487,, Oct. 2014, pp. 26-35.
Laprune, David , et al., "Highly Disperesed Nickel Particles Encapsulated in Multihollow Silicalite-1 Single Crystal Nanoboxes: Effects of Siliceous Deposits and Phosphorous Species on the Catalytic Performances", ChemCatChem, Sep. 2017, pp. 2297-2307.
Liang, Wenping , et al., "Surfactant Applications in Dispersion Systems", China Light Industry Press, Feb. 2003.
Roque-Malherbe, Rolando M.A., "Adsorption and Diffusion in Nanoporous Materials", Materials Chemistry, Mar. 5, 2007.
[English Translation] Notice of Reasons for Refusal dated Jun. 28, 2022 for Japanese Patent Application No. 2019-521318; pp all.
[English Translation] Notice of Reasons for Refusal dated Jun. 28, 2022 for Japanese Patent Application No. 2019-521319; pp all.
[English Translation] Notice of Reasons for Refusal dated Jun. 28, 2022 for Japanese Patent Application No. 2019-521320; pp. all.
[English Translation] Notice of Reasons for Refusal dated Jun. 28, 2022 for Japanese Patent Application No. 2019-521321; pp. all.
[English Translation] First Office Action dated May 16, 2022 for Chinese Patent Application No. 201880036071.3; pp. all.
[English Translation] First Office Action dated May 5, 2022 for Chinese Patent Application No. 201880036312.4; pp. all.
[English Translation] First Office Action dated May 7, 2022 for Chinese Patent Application No. 201880035210.0; pp. all.
[English Translation] Notice of Reasons for Refusal dated Jun. 6, 2022 for Japanese Patent Application No. 2019-521326; pp. all.
First Office Action dated May 6, 2022 for Australian Patent Application No. 2021202968; pp. all.
Dai, Chengyi, et al., "Hollow Zeolite encapsulated Ni—Pt bimetals for sintering and coking resistant dry reforming of methane", Journal of Materials Chemistry A, Jan. 1, 2015, 9 pages.
[Partial English Translation] Zhang, Yicheng , et al., "Advances in the catalysis of methanol to aromatics reaction", Chemical Industry and Engineering Progress, vol. 35 No. 3, Mar. 5, 2016, pp. 801-806.

[English Abstract] Zhang, Lian-Zhong , et al., "Preparation of Phenol and Acetone with Solid Acid Catalyst", [With Chemical World, Mar. 16, 2012, pp. 487-490.
[English Translation] First Office Action dated Aug. 3, 2022 for Chinese Patent Application No. 201880035569.8; pp. all.
[English Translation] First Office Action dated Aug. 3, 2022 for Chinese Patent Application No. 201880036313.9; pp. all.
[English Translation] Notice of Reasons for Refusal dated Aug. 16, 2022 for Japanese Patent Application No. 2019-521324; pp. all.
[English Translation] "Preparation and Application of Molecular Sieves", Edited by Shanghai Reagent Factory, Jun. 1976; pp. all.
[English Translation] First Office Action dated Apr. 20, 2022 for Chinese Patent Application No. 201880035803.7; pp. all.
[English Translation] Li, Jinlin , et al., "SBA-16 with Different Pore Size Supported Cobal Catalyst for Fischer-Tropsch Synthesis", Journal of South-Central University for Nationalities (National Science Edition); vol. 34 No. 4, Key Laboratory of Catalysis and Materials Science of the State, Ethnic Affairs Commission & Ministry of Education, Dec. 2015; pp. all.
[English Translation] Liu, Quansheng , et al., "Progress in Water-Gas-Shift Catalysts", Progress in Chemistry; vol. 17 No. 3; Institute of Chemical Engineering, Inner Mongolia University of Technology, Hohhot 010062, China, May 2005; pp. all.
[English Translation] First Office Action dated Jul. 11, 2022 for Chinese Patent Application No. 201880036382.X.
[English Translation] First Office Action dated Jul. 13, 2022 for Chinese Patent Application No. 201880035026.6.
[English Translation] Notice of Reasons for Refusal dated Aug. 3, 2022 for Japanese Patent Application No. 2019-521322.
[English Translation] Notice of Reasons for Refusal dated Aug. 3, 2022 for Japanese Patent Application No. 2019-521331.
[English Translation] The First Office Action dated Jul. 20, 2022 for Chinese Patent Application No. 201880035173.3.
[English Translation] The First Office Action dated Jul. 20, 2022 for Chinese Patent Application No. 201880035360.1.
Dai, Chengyi, et al., "Synthesis of Hollow Nanocubes and Macroporous Monoliths of Silicalite-1 by Alkaline Treatment", Chemistry of Materials, Oct. 7, 2013, pp. 4197-4205.
Miao, Tao , et al., "Highly dispersed nickel within mesochannels of SBA-15 for CO methanation with enhanced activity and excellent thermostability", Fuel, Journal vol. 188, No. 12; homepage: www.elsevier.com/locate/fuel, 2017, pp. 267-276.
[English Translation] Notice of Reasons for Refusal dated Sep. 27, 2022 for Japanese Patent Application No. 2019-521325; pp. all.
[English Translation] Notice of Reasons for Refusal dated Sep. 27, 2022 for Japanese Patent Application No. 2019-521334, pp. all.
[English Translation] Notice of Reasons for Refusal dated Sep. 27, 2022 for Japanese Patent Application No. 2019-521335, pp. all.
[English Translation] Notice of Reasons for Refusal for Japanese Patent Application No. 2019-521326 dated Nov. 25, 2022, pp. all.
[English Translation] Second Office Action for Chinese Patent Application No. 201880035803.7 dated Nov. 10, 2022, pp. all.
[English Translation] Second Office Action for Chinese Patent Application No. 201880036312.4 dated Nov. 10, 2022, pp. all.
[English Translation] Zhong, Bangke , "Catalysis i Fine chemical process", Sinopec Press; ISBN 7-80164-251-1, Aug. 2002, 4 pages.
[English Translation] Notice of Reasons for Refusal for Japanese Patent Application No. 2019-521325 dated Sep. 27, 2022, pp. all.
[English Translation] Notice of Reasons for Refusal for Japanese Patent Application No. 2019-521334, dated Sep. 27, 2022, pp. all.
[English Translation] Notice of Reasons for Refusal for Japanese Patent Application No. 2019-521335, dated Sep. 27, 2022, pp. all.
[English Translation] Second Office Action dated Dec. 23, 2022 in CN Application No. 201880035210.0; pp. all.
[English Translation] Second Office Action dated Jan. 5, 2023 in CN Application No. 201880035525.5; pp. all.
Office Action dated Dec. 18, 2022 for SA Application No. 519410677; pp. all.
Office Action dated Dec. 18, 2023 for SA Application No. 519410673; pp. all.
Office Action dated Dec. 26, 2022 for SA Application No. 519410680; pp. all.

(56) References Cited

OTHER PUBLICATIONS

Second Office Action dated Jan. 20, 2023 for CN Application No. 201880035360.1; pp. all.
Second Office Action dated Jan. 12, 2023 for CN Application No. 201880036382.X; pp. all.
Second Office Action dated Jan. 19, 2023 for CN Application No. 201880035017.7; pp. all.
Second Office Action dated Jan. 20, 2023 for CN Application No. 201880035026.6, pp. all.
Second Office Action dated Jan. 18, 2023 in CN Application No. 201880036313.9; pp. all.
Decision of Refusal for Japanese Patent Application No. 2019-521318, dated Feb. 1, 2023, pp. all.
Decision of Refusal for Japanese Patent Application No. 2019-521319, dated Feb. 1, 2023, pp. all.
Notice of Reasons for Refusal for Japanese Patent Application No. 2019-521320, dated Feb. 1, 2023, pp, all.
Notice of Reasons for Refusal for Japanese Patent Application No. 2019-521321, dated Feb. 1, 2023, pp. all.
[English Translation] Second Office Action dated Feb. 18, 2023 in CN Application No. 201880035173.3; pp. all.
[English Translation] Second Office Action dated Feb. 24, 2023 in CN Application No. 201880035569.8; pp. all.
[English Translation] Third Office Action dated Mar. 8, 2023 in CN Application No. 201880035803.7; pp. all.
[English Translation] Third Office Action dated Mar. 8, 2023 in CN Application No. 201880036312.4; pp. all.
[English Translation] Notice of Reasons for Refusal for Japanese Patent Application No. 2019-521322 dated Apr. 4, 2023, pp, all.
[English Translation] Notice of Reasons for Refusal for Japanese Patent Application No. 2019-521325 dated Apr. 4, 2023, pp, all.
[English Translation] Notice of Reasons for Refusal for Japanese Patent Application No. 2019-521331 dated Apr. 4, 2023, pp, all.
[English Translation] Notice of Reasons for Refusal for Japanese Patent Application No. 2019-521335 dated Apr. 4, 2023, pp, all.
[English Translation] Notice of Reasons for Refusal dated Mar. 22, 2023 in JP Application No. 2019-521324; pp, all.

* cited by examiner

STRUCTURED CATALYST FOR METHANOL REFORMING, METHANOL REFORMING DEVICE, METHOD FOR PRODUCING STRUCTURED CATALYST FOR METHANOL REFORMING, AND METHOD FOR PRODUCING AT LEAST ONE OF OLEFIN OR AROMATIC HYDROCARBON

CROSS REFERENCE TO RELATED APPLICATIONS

The present application is a continuation application of International Patent Application No. PCT/JP2018/021094 filed on May 31, 2018, which claims the benefit of Japanese Patent Application No. 2017-108613, filed on May 31, 2017. The contents of these applications are incorporated herein by reference in their entirety.

TECHNICAL FIELD

The present disclosure relates to a structured catalyst for methanol reforming including a support of a porous structure and a catalytic substance, a methanol reforming device, a method for producing a structured catalyst for methanol reforming, and a method for producing at least one of an olefin or an aromatic hydrocarbon.

BACKGROUND ART

Aromatic hydrocarbons, especially benzene, toluene and xylene are useful compounds used as raw materials in various fields. Currently, aromatic hydrocarbons are usually produced from petroleum. However, since petroleum resources are limited, development of an alternative method for producing aromatic hydrocarbons is desired.

Aromatic hydrocarbons can be produced, for example, from methanol as a raw material. As a catalyst used for a catalytic reaction using methanol as a raw material, for example, Japanese Patent Application Laid-Open No. 2009-255014 discloses ZSM-5 type zeolite having a crystal diameter of 100 nm or less. The use of this catalyst allows the production of an olefin from methanol.

Catalyst Society News No. 96, Nov. 1, 2016 discloses Ag/ZSM-5 and ZnP/ZSM-5 as catalysts used in producing p-xylene from methanol.

SUMMARY OF DISCLOSURE

Technical Problem

However, in the related art, when zeolites are used as catalysts, it is known that the catalytic function of zeolites will be deactivated over time. The cause of this is the aluminum element in the skeletal structure being removed by steam or the like generated during the reaction, the cokes that precipitate in association with the reaction adhering to the aluminum element, and the like.

An object of the present disclosure is to provide a highly active structured catalyst for methanol reforming that suppresses decline in a catalytic function and has excellent catalytic function, a methanol reforming device including the structured catalyst for methanol reforming, a method for producing a structured catalyst for methanol reforming, and a method for producing at least one of an olefin or an aromatic hydrocarbon.

Solution to Problem

As a result of diligent research to achieve the object described above, the present inventors have found that a structured catalyst that can suppress the decline in function of a solid acid and can realize a long lifetime can be obtained by including:

a support of a porous structure composed of a zeolite-type compound; and a catalytic substance present in the support, the support having channels communicating with each other, and the catalytic substance being a solid acid and being present at least in the channels of the support;

and thus completed the present disclosure based on such finding.

In other words, the summary configurations of the present disclosure are as follows.

[1] A structured catalyst for methanol reforming, including:

a support of a porous structure composed of a zeolite-type compound; and a catalytic substance present in the support, the support having channels communicating with each other, and the catalytic substance being a solid acid and present least in the channels of the support.

[2] The structured catalyst for methanol reforming according to [1], in which each of the channels has an enlarged pore portion, and the catalytic substance is at least embedded in the enlarged pore portion.

[3] The structured catalyst for methanol reforming according to [2], in which the enlarged pore portion communicates with a plurality of pores constituting any one of a one-dimensional pore, a two-dimensional pore, and a three-dimensional pore.

[4] The structured catalyst for methanol reforming according to [2], in which the solid acid is made of nanoparticles, and an average particle diameter of the nanoparticles is greater than an average inner diameter of the channels and is less than or equal to an inner diameter of the enlarged pore portion.

[5] The structured catalyst for methanol reforming according to [4], in which the average particle size of the nanoparticles is from 0.1 nm to 50 nm.

[6] The structured catalyst for methanol reforming according to [5], in which the average particle size of the nanoparticles is from 0.45 nm to 14.0 nm.

[7] The structured catalyst for methanol reforming according to [4], in which a ratio of the average particle size of the nanoparticles to the average inner diameter of the channels is from 0.06 to 500.

[8] The structured catalyst for methanol reforming according to [7], in which the ratio of the average particle size of the nanoparticles to the average inner diameter of the channels is from 0.1 to 36.

[9] The structured catalyst for methanol reforming according to [7], in which the ratio of the average particle size of the nanoparticles to the average inner diameter of the channels is from 1.7 to 4.5.

[10] The structured catalyst for methanol reforming according to [1], containing metal oxide nanoparticles of the solid acid and containing a metal element (M) of the metal oxide nanoparticles in an amount of from 0.5 to 2.5 mass % relative to the structured catalyst for methanol reforming.

[11] The structured catalyst for methanol reforming according to [1], in which the channels have any one of the one-dimensional pore, the two-dimensional pore, and the three-dimensional pore defined by a framework of the zeolite-type compound and the enlarged pore portion that is different from any one of the one-dimensional pore, the two-dimensional pore, and the three-dimensional pore, the average inner diameter of the channels is from 0.1 nm to 1.5 nm, and the inner diameter of the enlarged pore portion is from 0.5 nm to 50 nm.

[12] The structured catalyst for methanol reforming according to [1], further including at least one other catalytic substance held on an outer surface of the support.

[13] The structured catalyst for methanol reforming according to [12], in which a content of the catalytic substance present in the support is greater than a content of the at least one other catalytic substance held on the outer surface of the support.

[14] The structured catalyst for methanol reforming according to [1], in which the zeolite-type compound is a silicate compound.

[15] A methanol reforming device including the structured catalyst for methanol reforming described in [1].

[16] A method for producing a structured catalyst for methanol reforming, including:

a step of calcination of calcinating a precursor material (B) obtained by impregnating a precursor material (A), for obtaining a support of a porous structure composed of a zeolite-type compound, with a metal-containing solution; and a step of hydrothermal treatment of hydrothermal-treating a precursor material (C) obtained by calcinating the precursor material (B).

[17] The method fir producing a structured catalyst for methanol reforming according to [16], in which from 50 to 500 mass % of a non-ionic surfactant is added to the precursor material (A) before the step of calcination.

[18] The method for producing a structured catalyst for methanol reforming according to [16], in which the precursor material (A) is impregnated with the metal-containing solution by adding the metal-containing solution to the precursor material (A) in multiple portions before the step of calcination.

[19] The method for producing a structured catalyst for methanol reforming according to [16], in which in impregnating the precursor material (A) with the metal-containing solution before the step of calcination, an added amount of the metal-containing solution added to the precursor material (A), converted into a ratio of silicon (Si) constituting the precursor material (A) to a metal element (M) included in the metal-containing solution added to the precursor material (A) (a ratio of number of atoms Si/M), is adjusted to from 10 to 1000.

[20] The method for producing a structured catalyst for methanol reforming according to [16], in which in the step of hydrothermal treatment, the precursor material (C) and a structure directing agent are mixed.

[21] The method for producing a structured catalyst for methanol reforming according to [16], in which the step of hydrothermal treatment is performed under basic condition.

[22] A method for producing at least one of an olefin or an aromatic hydrocarbon, including adding methanol to the structured catalyst for methanol reforming according to [1].

[23] A method for producing at least one of an olefin or an aromatic hydrocarbon, including treating methanol with the methanol reforming device according to [15].

Advantageous Effects of Disclosure

The present disclosure provides a highly active structured catalyst for methanol reforming that suppresses the decline in catalytic function and has excellent catalytic function; and a methanol reforming device.

BRIEF DESCRIPTION OF DRAWINGS

FIG. 1A is a perspective view (partially shown in cross-section), and FIG. 1B is a partially enlarged cross-sectional view.

FIG. 2A is a diagram illustrating sieving capability, and FIG. 2B is a diagram explaining catalytic function.

DESCRIPTION OF EMBODIMENTS

Figure 1A:
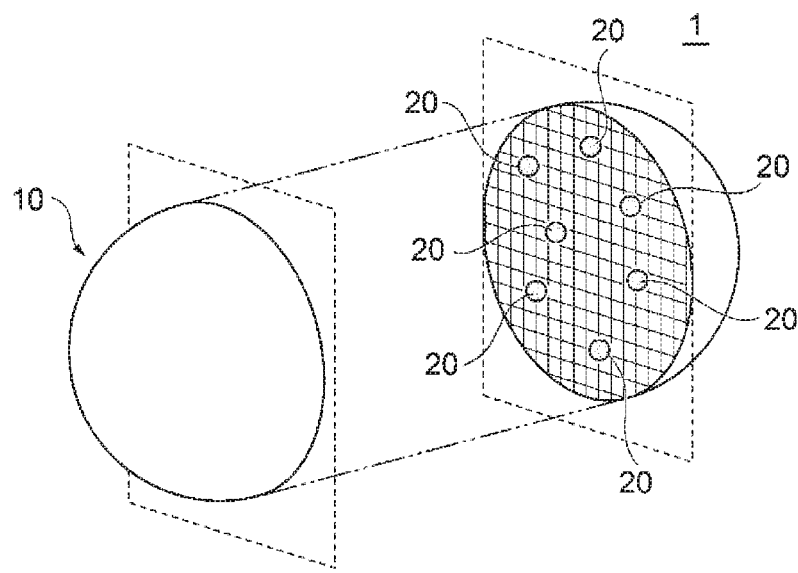
FIGS. 1A and 1B are diagrams schematically illustrating a structured catalyst for methanol reforming according to an embodiment of the present disclosure so that the inner structure can be understood.
Figure 1B:
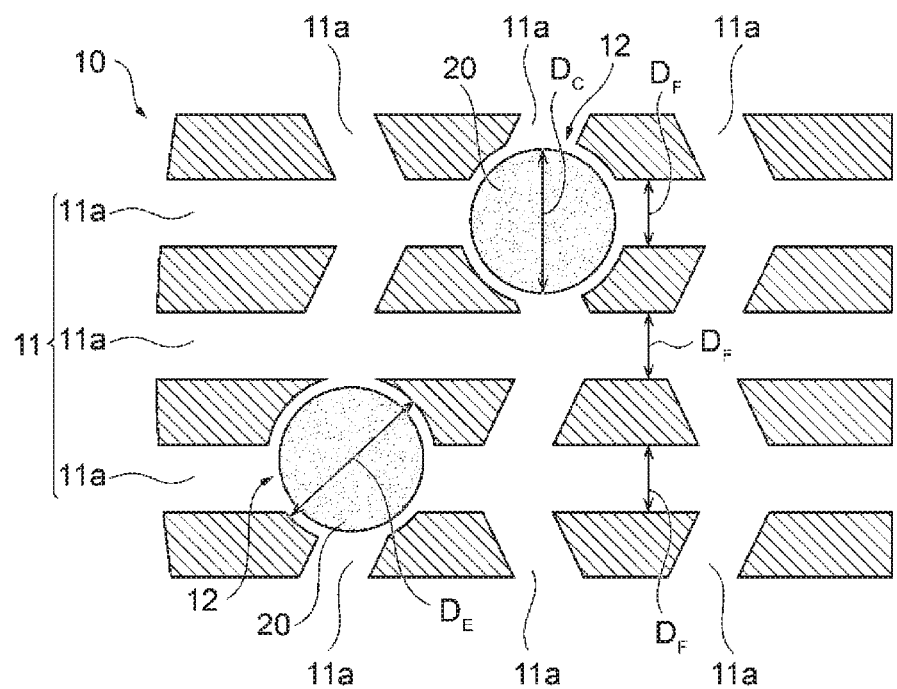

Hereinafter, embodiments of the present disclosure will be described in detail with reference to drawings.
Configuration of Structured Catalyst FIGS. 1A and 1B is a diagram schematically illustrating a configuration of a structured catalyst for methanol reforming (hereinafter referred to simply as "structured catalyst") according to an embodiment of the present disclosure. FIG. 1A is a perspective view (partially shown in cross-section), and FIG. 1B is a partially enlarged cross-sectional view. Note that the structured catalyst in FIGS. 1A and 1B is an example of the structured catalyst, and the shape, dimension, and the like of each of the configurations according to the present disclosure are not limited to those illustrated in FIGS. 1A and 1B.

As illustrated in FIG. 1A, a structured catalyst 1 includes a support 10 of a porous structure composed of a zeolite-type compound and a catalytic substance (solid acid) 20 present in the support 10. In the structured catalyst 1, a plurality of the solid acids 20, 20, . . . are embedded in the porous structure of the support 10.

The support 10 has a porous structure, and as illustrated in FIG. 1B, a plurality of pores 11a, 11a, . . . are preferably formed so as to have channels 11 communicating with each other. Here, the solid acid 20 is present at least in the channels 11 of the support 10 and is preferably held at least in the channels 11 of the support 10.

With such a configuration, movement of the solid acid 20 within the support 10 is restricted, and aggregation between the solid acids 20 and 20 is effectively prevented. As a result, the decrease in effective surface area as the solid acid 20 can be effectively suppressed, and the function of the solid acid 20 lasts for a long period of time. In other words, according to the structured catalyst 1, the decline in function due to aggregation of the solid acid 20 can be suppressed, and the life of the structured catalyst 1 can be extended. In addition, due to the long life time of the structured catalyst 1, the replacement frequency of the structured catalyst 1 can be reduced, and the amount of waste of the used structured catalyst 1 can be significantly reduced and thereby can save resources.

Typically, when the structured catalyst is used in a fluid (e.g., a heavy oil, or modified gas such as $NO_x$, etc.), it can be subjected to external forces from the fluid. In this case, if the solid acid is only held in the state of attachment to the outer surface of the support 10, there is a problem of easy detachment from the outer surface of the support 10 due to the influence of external force from the fluid. In contrast, in the structured catalyst 1, the solid acid 20 is present at least in the channels 11 of the support 10, and therefore, even if subjected to an external force caused by a fluid, the solid acid 20 is less likely to detach from the support 10. That is, when the structured catalyst 1 is in the fluid, the fluid flows into the channels 11 from the pores Ha of the support 10, so that the speed of the fluid flowing through the channels 11 is slower than the speed of the fluid flowing on the outer surface of the support 10 due to the flow path resistance (frictional force). Due to the influence of such flow path resistance, the pressure experienced by the solid acid 20 present in the channels 11 from the fluid is lower than the pressure at which the solid acid is received from the fluid outside of the support 10. As a result, detachment of the solid acid 20 present in the support 10 can be effectively suppressed, and the function of the solid acid 20 can be stably maintained over a long period of time. Note that the flow path resistance as described above is thought to be larger as the channels 11 of the support 10 have a plurality of bends and branches and as the interior of the support 10 becomes a more complex three-dimensional structure.

Preferably, the channels 11 have any one of a one-dimensional pore, a two-dimensional pore, and a three-dimensional pore defined by a framework of the zeolite-type compound; and an enlarged pore portion which is different from any one of the one-dimensional pore, the two-dimensional pore, and the three-dimensional pore. In this case, the solid acid 20 is preferably present at least in the enlarged pore portion 12 and is more preferably embedded at least in the enlarged pore portion 12. Here, the "one-dimensional pore" refers to a tunnel-type or cage-type pore forming a one-dimensional channel; or a plurality of tunnel-type or cage-type pores (a plurality of one-dimensional channels) forming a plurality of one-dimensional channels. Also, the "two-dimensional pore" refers to a two-dimensional channel in which a plurality of one-dimensional channels is connected two-dimensionally. The "three-dimensional pore" refers to a three-dimensional channel in which a plurality of one-dimensional channels are connected three-dimensionally.

As a result, the movement of the solid acid 20 within the support 10 is further restricted, and detachment of the solid acid 20 and aggregation between the solid acids 20, 20 can be further effectively prevented. Embedding refers to a state in which the solid acid 20 is included in the support 10. At this time, the solid acid 20 and the support 10 need not necessarily be in direct contact with each other, but the solid acid 20 may be indirectly held by the support 10 with other substances (e.g., a surfactant, etc.) interposed between h solid acid 20 and the support 10.

Although FIG. 1B illustrates the case in which the solid acid 20 is embedded in the enlarged pore portion 12, the solid acid 20 is not limited to this configuration only, and the solid acid 20 may be held in the channels 11 with a portion thereof protruding outward of the enlarged pore portion 12. Furthermore, the solid acid 20 may be partially embedded in a portion of the channels 11 other than the enlarged pore portion 12 (for example, an inner wall portion of the channels 11) or may be held by fixing or the like, for example.

Additionally, the enlarged pore portion 12 preferably communicates with the plurality of pores 11a, 11a constituting any one of the one-dimensional pore, the two-dimensional pore, and the three-dimensional pore. As a result, a separate channel different from the one-dimensional pore, the two-dimensional pore, or the three-dimensional pore is provided in the support 10, so the function of the catalytic substance 20 can be further exhibited.

Additionally, the channels 11 are formed three-dimensionally by including a branch portion or a merging portion within the support 10, and the enlarged pore portion 12 is preferably provided in the branch portion or the merging portion of the channels 11.

The average inner diameter $D_F$ of the channels 11 formed in the support 10 is calculated from the average value of the short diameter and the long diameter of the pore 11a constituting any one of the one-dimensional pore, the two-dimensional pore, and the three-dimensional pore. For example, it is from 0.1 nm to 1.5 nm and preferably from 0.5 nm to 0.8 nm.

An inner diameter $D_E$ of the enlarged pore portion 12 is from 0.5 nm to 50 nm, for example. The inner diameter $D_E$ is preferably from 1.1 nm to 40 nm and more preferably from 1.1 nm to 3.3 nm. For example, the inner diameter $D_E$ of the enlarged pore portion 12 depends on the pore diameter of the precursor material (A) described below and an average particle size $D_C$ of the solid acid 20 to be embedded. The inner diameter $D_E$ of the enlarged pore portion 12 is sized so that the enlarged pore portion 12 is able to embed the solid acid 20.

The support 10 is composed of a zeolite-type compound. Examples of zeolite-type compounds include zeolite analog compounds such as zeolites (alminosilicate salts), cation exchanged zeolites, silicate compounds such as silicalite, alminoborate salts, alminoarsenate salts, and germanate salts; and phosphate-based zeolite analog materials such as molybdenum phosphate. Among these, the zeolite-type compound is preferably a silicate compound.

The framework of the zeolite-type compound is selected from FAU type (Y type or X type), MTW type, MEI type (ZSM-5), FER type (ferrierite), LTA type (A type), MWW type (MCM-22), MOR type (inordenite), LTL type (L type), and BEA type (beta type). Preferably, it is MFI type and more preferably ZSM-5. A plurality of pores having a pore diameter corresponding to each framework is formed in the zeolite-type compound. For example, the maximum pore diameter of MFI type is 0.636 nm (6.36 Å), and the average pore diameter is 0.560 nm (5.60 Å).

In the following, the solid acid 20 will be described in detail.

When the solid acid 20 is made of nanoparticles, nanoparticles may be present in the channels 11 in the state of primary particles or present in the channels 11 in the state of secondary particles formed by aggregation of primary particles. In both cases, the average particle size $D_C$ of the nanoparticles is preferably greater than the average inner diameter $D_F$ of the channels 11 and is less than or equal to the inner diameter $D_E$ of the enlarged pore portion 12 ($D_F<D_C\le D_E$). Such solid acid 20 is suitably embedded in the enlarged pore portion 12 within the channels 11, and the movement of the solid acid 20 within the support 10 is restricted. Thus, even if the solid acid 20 is subjected to an external force from a fluid, movement of the solid acid 20 within the support 10 is suppressed, and it is possible to effectively prevent contact between the solid acids 20, 20, . . . embedded in the enlarged pore portions 12, 12, . . . dispersed in the channels 11 of the support 10.

When the solid acid 20 is made of nanoparticles, the average particle size $D_C$ of the nanoparticles 20 is preferably from 0.1 nm to 50 nm, more preferably 0.1 nm or more and less than 30 nm, further preferably from 0.45 nm to 14.0 nm, and particularly preferably from 1.0 nm to 3.3 nm for primary particles and secondary particles. Furthermore, the ratio ($D_C/D_F$) of the average particle size $D_C$ of the solid acid 20 to the average inner diameter $D_F$ of the channels 11 is preferably from 0.06 to 500, more preferably from 0.1 to 36, even more preferably from 1.1 to 36, and particularly preferably from 1.7 to 4.5.

Specific examples of the solid acid 20 include metal oxides and hydrates thereof, sulfides, metal salts, complex oxides, and heteropolyacids. The metal oxides include iron oxide ($FeO_x$), zinc oxide ZnO), aluminum oxide ($Al_2O_3$), zirconium oxide ($ZrO_2$), titanium oxide ($TiO_2$), selenium trioxide ($SeO_3$), selenium dioxide ($SeO_2$), tellurium trioxide ($TeO_3$), tellurium dioxide ($TeO_2$), tin oxide ($SnO_2$), manganese oxide ($Mn_2O_7$), technetium oxide ($Tc_2O_7$), and rhenium oxide ($Re_2O_7$). Examples of the sulfide include cadmium sulfide (CdS) and zinc sulfide (ZnS). Examples of the metal salt include magnesium sulfate ($MgSO_4$), iron sulfate ($FeSO_4$), and aluminum chloride ($AlCl_3$). Examples of the complex oxide include $SiO_2$—$TiO_2$, $SiO_2$—MgO, and $TiO_2$—$ZrO_2$. Furthermore, examples of the heteropolyacid include phosphotungstic acid, silicotungstic acid, phosphomolybdic acid, and silicomolybdic acid. These solid acids 20 may be used alone or in combination of a plurality of types of them. The solid acid 20 is distinguished from a zeolite-type compound constituting the support 10. The solid acid 20 does not include, for example, zeolite.

A metal element (M) of the solid acid 20 is preferably contained in from 0.5 to 2.5 mass % relative to the structured catalyst 1 and more preferably from 0.5 to 1.5 mass % relative to the structured catalyst 1. For example, when the metal element (M) is Zr, the content of the Zr element (mass %) is expressed as [(mass of Zr element)/(mass of all elements in the structured catalyst 1)]×100. When a plurality of metals is contained in the solid acid, the metal element (M) means the total mass of the plurality of metals.

Furthermore, the ratio of silicon (Si) constituting the support 10 to the metal element (M) constituting the solid acid 20 (the ratio of number of atoms Si/M) is preferably from 10 to 1000 and more preferably from 50 to 200. In a case where the ratio is greater than 1000, the activity is low, so that the action as the solid acid may not be sufficiently obtained. On the other hand, in a case where the ratio is smaller than 10, the proportion of the solid acid 20 becomes too large, and the strength of the support 10 tends to decrease. Note that the solid acid 20 herein refers to a solid acid that is held or supported in the support 10 and does not include the solid acid adhered to the outer surface of the support 10.

Function of Structured Catalyst

As described above, the structured catalyst 1 includes the support 10 of a porous structure and at least one solid acid 20 present in the support 10. The structured catalyst 1 exhibits a function according to the function of the solid acid 20 upon contact of the solid acid 20 present in the support 10 with a fluid. Specifically, the fluid in contact with an outer surface 10a of the structured catalyst 1 flows into the support 10 through the pore 11a formed in the outer surface 10a and guided into the channels 11, moves through the channels 11, and exits to the exterior of the structured catalyst 1 through the other pore 11a. In the pathway through which the fluid travels through the channels 11, the contact with the solid acid 20 present in the channels 11 results in a reaction (e.g., a catalytic reaction) according to the function of the solid acid 20. In addition, the structured catalyst 1 has molecular sieving capability due to the porous structure of the support.

Figure 2A:
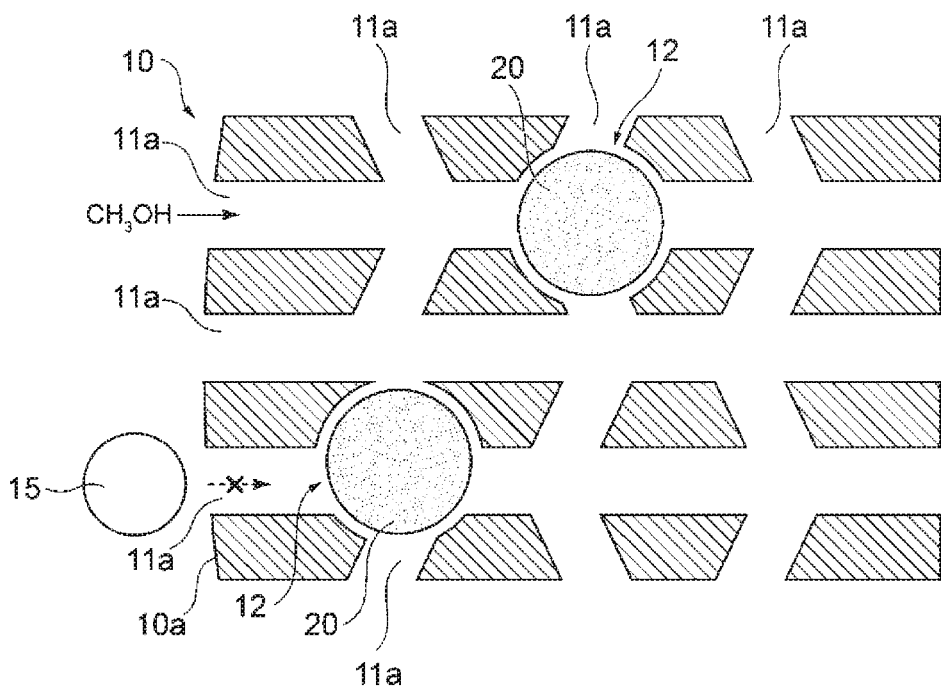
FIGS. 2A and 2B are partial enlarged cross-sectional views for explaining an example of the function of the structured catalyst for methanol reforming of FIGS. 1A and 1B.

First, the molecular sieving capability of the structured catalyst 1 is described using FIG. 2A in which the fluid is, for example, a methanol-containing gas. Note that "methanol-containing gas" refers to a mixed gas containing methanol and a gas other than methanol.

As illustrated in FIG. 2A, methanol ($CH_3OH$) composed of molecules having a size that is less than or equal to the pore diameter of the pore 11a, in other words, less than or equal to the inner diameter of the channels 11, can flow into the support 10. On the other hand, a gas component 15 composed of molecules having a size exceeding the pore diameter of the pore 11a cannot flow into the support 10. In this way, when the fluid contains a plurality of types of compounds, the reaction of the gas component 15 that cannot flow into the support 10 is restricted, while methanol capable of flowing into the support 10 is allowed to react.

Of the compounds produced in the support 10 by the reaction, only compounds composed of molecules having a size less than or equal to the pore diameter of the pore 11a can exit through the pore 11a to the exterior of the support 10 and are obtained as reaction products. On the other hand, a compound that cannot exit to the exterior of the support 10 from the pore 11a can be released to the exterior of the support 10 after being converted into a compound composed of molecules sized to be able to exit to the exterior of the support 10. In this way, a specified reaction product can be selectively obtained by using the structured catalyst 1.

Figure 2B:
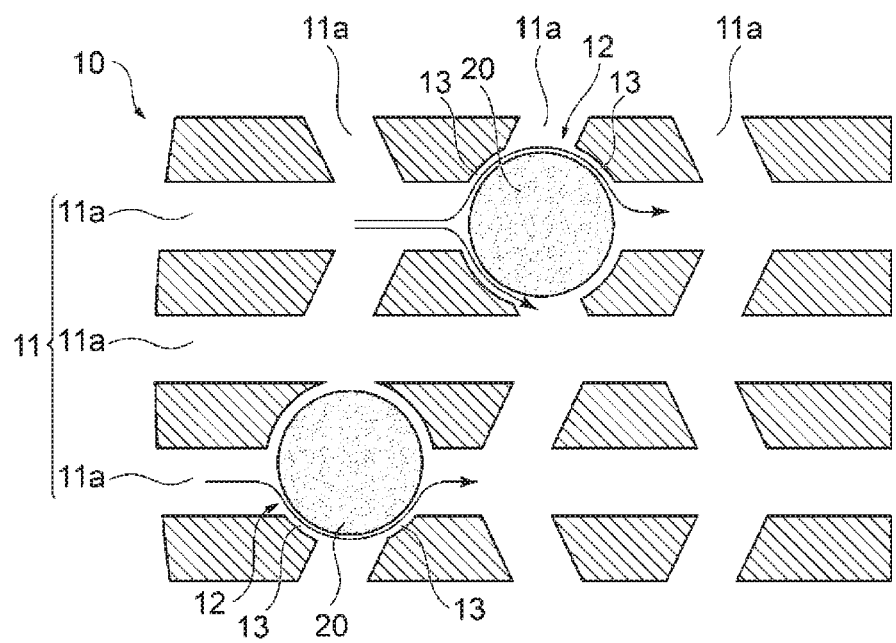

In the structured catalyst 1, as illustrated in FIG. 2B, the solid acid 20 is embedded in the enlarged pore portion 12 of the channels 11. When the solid acid 20 is made of nanoparticles, the average particle size $D_C$ of the solid acid 20 is larger than the average inner diameter $D_F$ of the channels 11 and smaller than the inner diameter $D_E$ of the enlarged pore portion 12 ($D_F<D_C<D_E$), a small channel 13 is firmed between the solid acid 20 and the enlarged pore portion 12. Thus, as indicated by the arrow in FIG. 2B, the fluid that has flown into the small channel 13 comes into contact with the solid acid 20. In the present embodiment, when the methanol flowing into the small channel 13 comes into contact with the solid acid 20, olefins are produced. The olefins produced here are, for example, C2-C4 olefins, and specifically ethylene, propylene, and the like. Furthermore, aromatic hydrocarbons such as benzene, toluene, and xylene are also produced. Because each solid acid 20 is embedded in the enlarged pore portion 12, movement within the support 10 is restricted. As a result, aggregation between the solid acids 20 in the support 10 is prevented. As a result, a large contact area between the solid acid 20 and methanol can be stably maintained. Thus, the solid acid 20 has excellent catalytic function. The use of the structured catalyst 1 allows efficient production of olefins and aromatic hydrocarbons using methanol as a raw material.

Method for Producing Structured Catalyst

Figure 3:
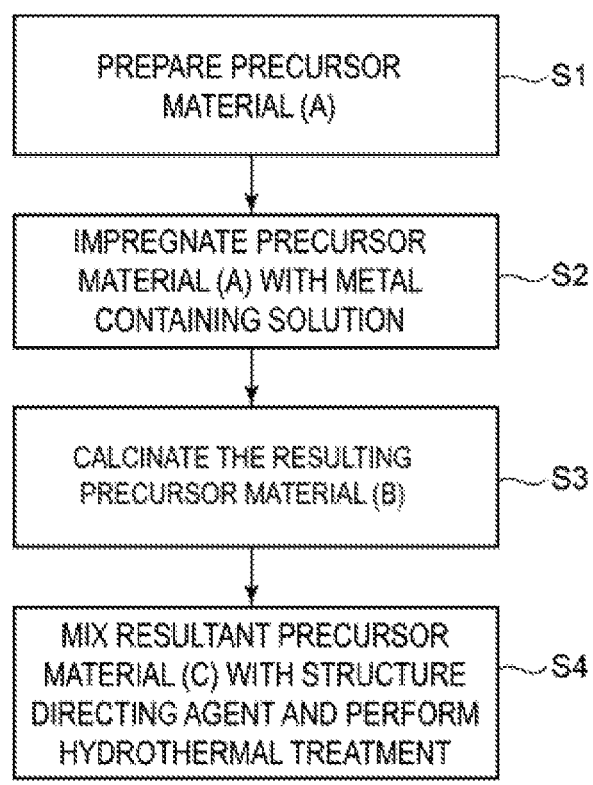
FIG. 3 is a flowchart illustrating an example of a method for producing the structured catalyst for methanol reforming of FIGS. 1A and 1B.

FIG. 3 is a flowchart illustrating a method for producing the structured catalyst 1 of FIGS. 1A and 1B. An example of the method for producing the structured catalyst will be described below, in which the solid acid present in the support is made of metal oxide nanoparticles.

Step S1: Step of Preparation

As shown in FIG. 3, firstly, the precursor material (A) for obtaining a support of a porous structure composed of a zeolite-type compound is prepared. The precursor material (A) is preferably a regular mesopore material and can be appropriately selected according to the type (composition) of the zeolite-type compound constituting the support of the structured catalyst.

Here, when the zeolite-type compound constituting support of the structured catalyst is a silicate compound, the regular mesopore material is preferably a compound including a Si—O skeleton in which pores having a pore diameter of from 1 to 50 nm are uniformly sized and regularly developed one-dimensionally, two-dimensionally, or three-dimensionally. While such a regular mesopore material is obtained as a variety of synthetic materials depending on the synthetic conditions. Specific examples of the synthetic material include SBA-1, SBA-15, SBA-16, KIT-6, FSM-16, and MCM-41. Among them, MCM-41 is preferred. Note that the pore diameter of SBA-1 is from 10 to 30 nm, the pore diameter of SBA-15 is from 6 to 10 nm, the pore diameter of SBA-16 is 6 nm, the pore diameter of KIT-6 is 9 nm, the pore diameter of FSM-16 is from 3 to 5 nm, and the pore diameter of MCM-41 is from 1 to 10 nm. Examples of such a regular mesopore material include mesoporous silica, mesoporous aluminosilicate, and mesoporous metallosilicate.

The precursor material (A) may be a commercially available product or a synthetic product. When the precursor material (A) is synthesized, it can be synthesized by a known method for synthesizing a regular mesopore material. For example, a mixed solution including a raw material containing the constituent elements of the precursor material (A) and a molding agent for defining the structure of the precursor material (A) is prepared, and the pH is adjusted as necessary to perform hydrothermal treatment (hydrothermal synthesis). Thereafter, the precipitate (product) obtained by hydrothermal treatment is recovered (e.g., filtered), washed and dried as necessary, and then calcinated to obtain the precursor material (A) which is a powdered regular mesopore material. Here, examples of the solvent of the mixed solution include water, organic solvents such as alcohols, and mixed solvents thereof. In addition, the raw material is selected according to the type of the support, and examples thereof include silica agents such as tetraethoxysilane (TEOS); fumed silica; and quartz sand. In addition, various types of surfactants, block copolymers, and the like can be used as the molding agent, and it is preferably selected depending on the type of the synthetic materials of the regular mesopore material. For example, a surfactant such as hexadecyltrimethylammonium bromide is preferable when producing MCM-41. The hydrothermal treatment can be performed at from 0 to 2000 kPa at from 80 to 800° C. for from 5 hours to 240 hours in a sealed container. For example, the calcination treatment may be performed in air, at from 350 to 850° C. for from 2 hours to 30 hours.

Step S2: Step of Impregnation

The prepared precursor material (A) is then impregnated with the metal-containing solution to obtain a precursor material (B).

The metal-containing solution is a solution containing a metal component (for example, a metal ion) corresponding to the metal element (NI) constituting the metal oxide nanoparticles of the structured catalyst and can be prepared, for example, by dissolving a metal salt containing the metal element (M) in a solvent. Examples of the metal salt include chlorides, hydroxides, oxides, sulfates, and nitrates. Among these, nitrates are preferable. Examples of the solvent include water, organic solvents such as alcohols, and mixed solvents thereof.

The method for impregnating the precursor material (A) with the metal-containing solution is not particularly limited; however, for example, the metal-containing solution is preferably added in portions in a plurality of times while mixing the powdered precursor material (A) before the step of calcination described below. In addition, the surfactant is preferably added to the precursor material (A) as the additive before adding the metal-containing solution to the precursor material (A) from the perspective of allowing the metal-containing solution to enter the pores of the precursor material (A) more easily. It is believed that such additives serve to cover the outer surface of the precursor material (A) and inhibit the subsequently added metal-containing solution from adhering to the outer surface of the precursor material (A), making it easier for the metal-containing solution to enter the pores of the precursor material (A).

Examples of the additive include non-ionic surfactants such as polyoxyethylene alkyl ethers such as polyoxyethylene oleyl ether; and polyoxyethylene alkylphenyl ether. It is believed that these surfactants do not adhere to the interior of the pores because their molecular size is large, cannot enter the pores of the precursor material (A), and will not interfere with the penetration of the metal-containing solution into the pores. As the method for adding the non-ionic surfactant, for example, it is preferable to add from 50 to 500 mass % of the non-ionic surfactant to the precursor material (A) prior to the step of calcination described below. If the added amount of the non-ionic surfactant to the precursor material (A) is less than 50 mass %, the aforementioned suppressing action will not easily occur, and when more than 500 mass % of the non-ionic surfactant is added to the precursor material (A), the viscosity is too high, which is not preferable. Thus, the added amount of the non-ionic surfactant to the precursor material (A) is a value within the range described above.

Furthermore, the added amount of the metal-containing solution added to the precursor material (A) is preferably adjusted as appropriate in consideration of the amount of the metal element (M) contained in the metal-containing solution with which the precursor material (A) is impregnated (that is, the amount of the metal element (M) present in the precursor material (B)). For example, prior to the step of calcination described below, the added amount of the metal-containing solution added to the precursor material (A), converted into a ratio of silicon (Si) constituting the precursor material (A) to the metal element (M) included in the metal-containing solution added to the precursor material (A) (the ratio of number of atoms Si/M), is preferably adjusted from to 10 to 1000 and more preferably from 50 to 200. For example, before adding the metal-containing solution to the precursor material (A), when a surfactant is added to the precursor material (A) as an additive and when the added amount of the metal-containing solution added to the precursor material (A), converted into the ratio of number of atoms Si/M, is from 50 to 200, from 0.5 to 2.5 mass % of the metal element (M) of the metal oxide nanoparticles can be included in the structured catalyst. In the state of the precursor material (B), the amount of the metal element (M) present within the pores is generally proportional to the added amount of the metal-containing solution added to the precursor material (A) in a case where the metal concentration of the metal-containing solution, the presence or absence of additives, and other conditions such as temperature, pressure, and the like are the same. The amount of metal element (M) present in the precursor material (B) is also in a proportional relationship to the amount of metal element constituting the metal oxide nanoparticles present in the support of the structured catalyst. Thus, by controlling the added amount of the metal-containing solution added to the precursor material (A) to the range described above, the pores of the precursor material (A) can be sufficiently impregnated with the metal-containing solution, and thus the amount of the metal oxide nanoparticles present in the support of the structured catalyst can be adjusted.

After impregnating the precursor material (A) with the metal-containing solution, a washing treatment may be performed as necessary. Examples of the washing solution include water, organic solvents such as alcohols, and mixed solvents thereof. Furthermore, the precursor material (A) is preferably impregnated with the metal-containing solution, and after the washing treatment is performed as necessary, the precursor material (A) is further subjected to drying treatment. Drying treatments include overnight natural drying and high temperature drying at 150° C. or lower. Note that when calcination treatment described below is performed in the state in which there is a large amount of moisture remaining in the metal-containing solution and the washing solution in the precursor material (A), the skeletal structure of the regular mesopore material of the precursor material (A) may be broken, and thus it is preferable to dry them sufficiently.

Step S3: Step of Calcination

Next, a precursor material (C) is obtained by calcinating the precursor material (B) obtained by impregnating the precursor material (A), for obtaining the support of a porous structure composed of a zeolite-type compound, with the metal-containing solution.

For example, the calcination treatment is preferably performed in air, at from 350 to 850° C. for from 2 hours to 30 hours. The metal component that has entered the pores of the regular mnesopore material undergoes crystal growth by such calcination treatment, and metal oxide nanoparticles are formed in the pores.

Step S4: Step of Hydrothermal Treatment

A mixed solution of the precursor material (C) and a structure directing agent is then prepared, and the precursor material (C) obtained by calcinating the precursor material (B) is hydrothermal-treated to obtain a structured catalyst.

The structure directing agent is a molding agent for directing the skeletal structure of the support of the structured catalyst and may be, for example, a surfactant. The structure directing agent is preferably selected according to the skeletal structure of the support of the structured catalyst and is preferably a surfactant such as tetramethylammonium bromide (TMABr), tetraethylammonium bromide (TEABr), or tetrapropylammonium bromide (TPABr).

The mixing of the precursor material (C) and the structure directing agent may be performed during the step of hydrothermal treatment or may be performed before the step of hydrothermal treatment. Furthermore, the method for preparing the mixed solution is not particularly limited, and the precursor material (C), the structure directing agent, and the solvent may be mixed simultaneously, or each of the dispersion solutions may be mixed after the precursor material (C) and the structure directing agent are each dispersed in individual solutions. Examples of the solvent include water, organic solvents such as alcohols, and mixed solvents thereof. In addition, it is preferable that the pH of the mixed solution is adjusted using an acid or a base before performing the hydrothermal treatment.

The hydrothermal treatment can be performed by a known method. For example, the hydrothermal treatment can be preferably performed at from 0 to 2000 kPa at from 80 to 800° C. for from 5 hours to 240 hours in a sealed container. Furthermore, the hydrothermal treatment is preferably performed under basic condition.

Although the reaction mechanism here is not necessarily clear, by performing hydrothermal treatment using the precursor material (C) as a raw material, the skeletal structure as the regular mesopore material of the precursor material (C) becomes increasingly disrupted. However, the action of the structure directing agent forms a new skeletal structure (porous structure) of the support of the structured catalyst while maintaining the position of the metal oxide nanoparticles within the pores of the precursor material (C). The structured catalyst obtained in this way includes a support of a porous structure and metal oxide nanoparticles present in the support, the support has channels in which a plurality of pores communicate with each other by the porous structure, and at least a portion of the metal oxide nanoparticles is held in the channels of the support.

Furthermore, in the present embodiment, in the step of hydrothermal treatment, a mixed solution in which the precursor material (C) and the structure directing agent are mixed is prepared, and the precursor material (C) is subjected to hydrothermal treatment. Not only limited to this, the precursor material (C) may be subjected to hydrothermal treatment without mixing the precursor material (C) and the structure directing agent.

The precipitate (structured catalyst) obtained after hydrothermal treatment is preferably washed, dried, and calcinated as necessary after recovery (e.g., filtration). Examples of the washing solution that can be used include water, an organic solvent such as an alcohol, or a mixed solution thereof. Drying treatments include overnight natural drying and high temperature drying at 150° C. or lower. Note that when calcination treatment is performed in the state in which there is a large amount of moisture remaining in the precipitate, the skeletal structure as a support of the structured catalyst may be broken, and thus it is preferable to dry the precipitate sufficiently. For example, the calcination treatment may be performed in air at from 350 to 850° C. for from 2 hours to 30 hours. Such calcination treatment burns out the structure directing agent that has been attached to the structured catalyst. Furthermore, the structured catalyst can be used as is without subjecting the recovered precipitate to calcination treatment, depending on the intended use. For example, in a case where the environment in which the structured catalyst is used is a high temperature environment of oxidizing condition, exposing the structured catalyst to the usage environment for a period of time allows the structure directing agent to be burned out. In this case, the same structured catalyst as when subjected to calcination treatment is obtained, so it is not necessary to perform the calcination treatment.

Modified Example of Structured Catalyst 1

Figure 4:
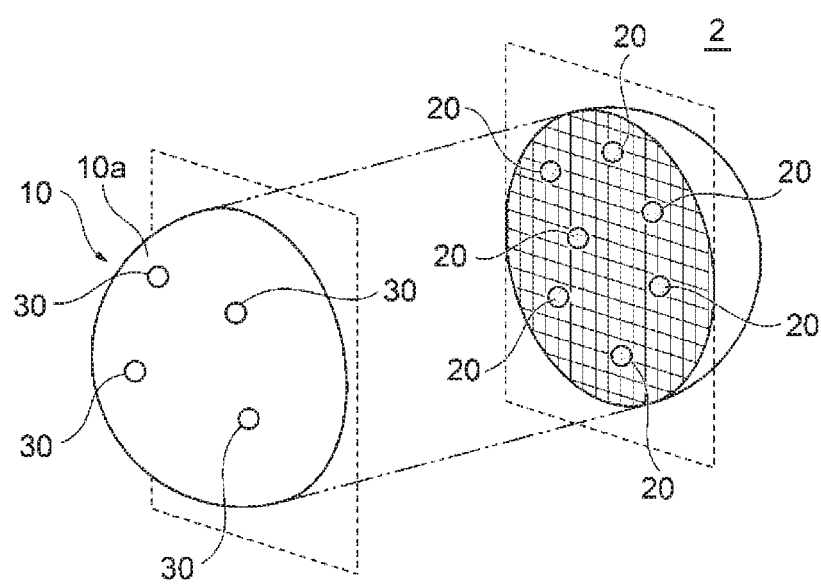
FIG. 4 is a schematic view illustrating a modified example of the structured catalyst for methanol reforming 1 in FIGS. 1A and 1B.

FIG. 4 is a schematic view illustrating a modified example of the structured catalyst 1 in FIGS. 1A and 1B.

Although the structured catalyst 1 of FIGS. 1A and 1B includes the support 10 and the solid acid 20 present in the support 10, the structured catalyst 1 is not limited to this configuration. For example, as illustrated in FIG. 4, the structured catalyst 2 may further include at least one other catalytic substance 30 held on the outer surface 10a of the support 10.

The catalytic substance 30 is a substance that exhibits one or more catalytic capacities. The catalytic capacity of the other catalytic substance 30 may be the same or different from the catalytic capacity of the solid acid 20. The catalytic substance 30 may be a solid acid or a substance other than a solid acid. When the catalytic substance 30 is a solid acid, the catalytic substance 30 may be the same substance as the solid acid 20 or may be a different substance. When the catalytic substance 30 is a solid acid, the content of the solid acid held in the structured catalyst 2 can be increased, and the catalytic activity of the solid acid can be further promoted.

In this case, the content of the solid acid 20 present in the support 10 is preferably greater than that of the catalytic substance 30 held on the outer surface 10a of the support 10. As a result, the catalytic capacity of the solid acid 20 held in the support 10 becomes dominant, and the catalytic capacity of the solid acid stably exhibited.

Hereinbefore, the structured catalyst according to the present embodiments has been described, but the present disclosure is not limited to the above embodiments, and various modifications and changes are possible on the basis of the technical concept of the present disclosure.

For example, methanol may be further added to the structured catalyst to produce at least one of an olefin or an aromatic hydrocarbon.

Additionally, a methanol reforming device including the structured catalyst may be provided. The use of the structured catalyst in a catalytic reaction using such a device allows the same effects as described above to be achieved. In this case, at least one of an olefin or an aromatic hydrocarbon may be produced by treating methanol with the methanol reforming device.

In addition, the catalyst described above may be used as a structured catalyst for fluid catalytic cracking to produce gasoline from bottom oil. In this case, the structured catalyst for fluid catalytic cracking includes a support of a porous structure composed of a zeolite-type compound and at least one type of metal nanoparticles present in the support, the support having channels communicating with each other, and the metal nanoparticles including a structured catalyst held in at least an enlarged pore portion of the channels of the support. For example, when the structured catalyst or catalytic molding has the shape and dimensions described above, for example, clogging of the catalyst layer by impurities and fractions can be prevented in the production of high octane gasoline by decomposing high boiling point hydrocarbons such as vacuum gas oil and atmospheric residual oil. Furthermore, gasoline may be produced by adding bottom oil to the structured catalyst for fluid catalytic cracking.

Furthermore, gasoline may be produced by treating bottom oil with a device for fluid catalytic cracking including a structured catalyst for fluid catalytic cracking. Additionally, for example, a device including the structured catalyst for fluid catalytic cracking may be provided. Examples of the device include a device for fluid catalytic cracking (FCC), and a propylene rectification device or a desulfurization device for cracked gasoline including the FCC device. The use of the structured catalyst for fluid catalytic cracking allows the same effects as described above to be achieved.

EXAMPLES

Examples 1 to 298

Synthesis of Precursor Material (A)

A mixed aqueous solution was prepared by mixing a silica agent (tetraethoxysilane (TEOS), available from Wako Pure Chemical Industries, Ltd.) and a surfactant as the molding agent. The pH was adjusted as appropriate, and hydrothermal treatment was performed at from 80 to 350° C. for 100 hours in a sealed container. Thereafter, the produced precipitate was filtered out, washed with water and ethanol, and then calcinated in air at 600° C. for 24 hours to obtain the precursor material (A) of the type and having the pore diameter shown in Tables 1 to 6. Note that the following surfactant was used in accordance with the type of the precursor material (A) ("precursor material (A): surfactant").

MCM-41: Hexadecyltrimethylammonium bromide (CTAB) (available from Wako Pure Chemical Industries, Ltd.)
SBA-1: Pluronic P123 (available from BASF)
Making of Precursor Materials (B) and (C)

Next, a metal-containing aqueous solution was prepared by dissolving a metal salt containing the metal element (M) in water according to the metal element (M) constituting the solid acid nanoparticles of the type shown in Tables 1 to 6. Note that the metal salt was used in accordance with the type of solid acid nanoparticles ("solid acid nanoparticles: metal salt").

$ZnO_x$: Zinc nitrate hexahydrate (available from Wako Pure Chemical Industries, Ltd.)
$AlO_x$: Aluminum nitrate nonahydrate (available Wako Pure Chemical Industries, Ltd.)
$ZrO_x$: Zirconium nitrate dihydrate (available from Wako Pure Chemical Industries, Ltd.)
$FeO_x$: Iron (III) nitrate nonahydrate (available from Wako Pure Chemical Industries, Ltd.)

Next, a metal-containing aqueous solution was added to the powdered precursor material (A) in portions and dried at room temperature (20° C.±10° C.) for 12 hours or longer to obtain the precursor material (B).

Note that when the presence or absence of additives shown in Tables 1 to 6 is "yes", pretreatment, in which an aqueous solution of polyoxyethylene (15) oleyl ether (NIKKOL BO-15 V, available from Nikko Chemicals Co., Ltd.) is added as the additive to the precursor material (A) before adding the metal-containing aqueous solution, was performed, and then the metal-containing aqueous solution was added as described above. Note that when "no" is used in the presence or absence of additives, pretreatment with an additive such as that described above was not performed.

Furthermore, the added amount of the metal-containing aqueous solution added to the precursor material (A) was adjusted to become the value in Tables 1 to 6, converted into a ratio of silicon (Si) constituting the precursor material (A) to the metal element (M) included in the metal-containing aqueous solution (the ratio of number of atoms Si/M).

Next, the precursor material (B) impregnated with the metal-containing aqueous solution obtained as described above was calcinated in air at 600° C. for 24 hours to obtain the precursor material (C).
Synthesis of Structured Catalyst The precursor material (C) obtained as described above and the structure directing agent shown in Tables 1 to 6 were mixed to produce a mixed aqueous solution and subjected to hydrothermal treatment in a sealed container under the conditions of at from 80 to 350° C. and the pH and time shown in Tables 1 to 6. Thereafter, the produced precipitate was filtered off, washed with water, dried at 100° C. for 12 hours or longer, and then calcinated in air at 600° C. for 24 hours, thereby obtaining the catalytic structural bodies having the supports and solid acid nanoparticles shown in Tables 1 to 6 (Examples 1 to 298).

Comparative Example 1

In Comparative Example 1, cobalt oxide powder (II, III) having an average particle size of 50 nm or less (available from Sigma-Aldrich Japan LLC) was mixed with WI type silicalite, and a catalytic structural body in which cobalt oxide nanoparticles were attached as the catalytic substance to the outer surface of the silicalite as the support was obtained. MFI type silicalite was synthesized in the similar manner as in Examples 52 to 57 except for a step of adding a metal.

Comparative Example 2

In Comparative Example 2, MFI type silicalite was synthesized in the similar manner as in Comparative Example 1 except that a step of attaching the cobalt oxide nanoparticles was omitted.

Comparative Example 3

A structured catalyst was obtained in the same manner as in Comparative Example 1 except that aluminum oxide nanoparticles (available from Wako Pure Chemical Industries, Ltd.) were adhered to the surface as solid acid nanoparticles.
Evaluation Various characteristic evaluations were performed on the catalytic structural bodies of Examples 1 to 298 and Comparative Examples 1 and 3; and the silicalite of Comparative Example 2 under the conditions described below.
[A] Cross-Sectional Observation Observation samples were made using a pulverization method for the catalytic structural bodies of Examples 1 to 298 and Comparative Examples 1 and 3; and the silicalite of Comparative Example 2, and the cross-sectional observation was performed using a transmission electron microscope (TEM) (TITAN G2, available from FEI).

As a result, it was confirmed that, in the structured catalyst of the example described above, solid acid nanoparticles were present and held in the support made of silicalite or zeolite. On the other hand, in the structured catalyst of Comparative Example 3, the solid acid nanoparticles were only attached to the outer surface of the support and were not present in the support.

In addition, of the examples described above, for the structured catalyst including $ZrO_x$ as the solid acid nanoparticles, the cross-section was cut by FIB (focused ion beam) processing, and cross-section element analysis was performed using SEM (SU8020, available from Hitachi High-Technologies Corporation) and EDX (X-Max, available from HORIBA, Ltd.). As a result, elements Zr were detected from inside the support.

It was confirmed that $ZrO_x$ nanoparticles were present in the support from the results of the cross-sectional observation using TEM and SEM/EDX.
[B] Average Inner Diameter of the Channels of the Support and Average Particle Size of Solid Acid Nanoparticles In the TEM image taken by the cross-sectional observation performed in evaluation [A] above, 500 channels of the support were randomly selected, the respective major diameter and the minor diameter were measured, the respective inner diameters were calculated from the average values (N=500), and the average value of the inner diameter was determined to be the average inner diameter $D_F$ of the channels of the support. In addition, also for the solid acid nanoparticles, 500 solid acid nanoparticles were randomly selected from the TEM image, the respective particle sizes were measured (N=500), and the average value thereof was determined to be the average particle size $D_C$ of the solid acid nanoparticles. The results are shown in Tables 1 to 6.

Also, SAXS (small angle X-ray scattering) was used to analyze the average particle size and dispersion status of the solid acid. Measurements by SAXS were performed using a-SPring-8 beam line BL19B2. The obtained SAXS data was fitted with a spherical model using the Guinier approximation method, and the particle size was calculated. The particle size was measured for the structured catalyst in which the metal oxide of the solid acid is iron oxide nanoparticles. Furthermore, as a comparative reference, a commercially available iron oxide nanoparticles (available from Wako) was observed and measured by SEM.

As a result, in commercial products, various sizes of iron oxide nanoparticles were randomly present in a range of particle sizes of approximately from 50 nm to 400 nm, whereas in the measurement results of SAXS, scattering peaks with particle sizes of 10 nm or less were also detected in the catalytic structural bodies of each example having an average particle size of from 1.2 nm to 2.0 nm determined from the TEM image. From the results of SAXS measurement and the SEM/EDX cross-sectional measurement, it was found that a solid acid having a particle size of 10 nm or less was present in the support in a markedly highly dispersed state with a uniform particle size.
[C] Relationship Between the Added Amount of the Metal-Containing Solution and the Amount of Metal Embedded in the Support A structured catalyst in which metal oxide nanoparticles were embedded in the support at an added amount of the ratio of number of atoms of Si/M=50, 100, 200, 1000 (M=Al, Zr, Zn, and Fe) was produced, and then the amount of metal (mass %) that was embedded in the support of the structured catalyst produced at the above added amount was measured. Note that in the present measurement, the functional structural bodies having the ratio of number of atoms of Si/M=100, 200, and 1000 were produced by adjusting the added amount of the metal-containing solution in the same manner as the catalytic structural bodies having the ratio of number of atoms of Si/M=100, 200, and 1000 of Examples 1 to 298, and the catalytic structural bodies having the ratio of number of atoms of Si/M=50 were produced in the same manner as the catalytic structural bodies having the ratio of number of atoms of Si/M=100, 200, and 1000, except that the added amount of the metal-containing solution was changed.

The amount of metal was quantified by ICP (radio frequency inductively coupled plasma) alone or in combination with ICP and XRF (fluorescence X-ray analysis). XRF (energy dispersive fluorescent x-ray analyzer "SEA1200VX", available from SII Nanotechnology) was performed under conditions of a vacuum atmosphere, an accelerating voltage 15 kV (using a Cr filter), or an accelerating voltage 50 kV (using a Pb filter).

XRF is a method for calculating the amount of metal present in terms of fluorescence intensity, and XRF alone cannot calculate a quantitative value (in terms of mass %). Therefore, the metal content of the structured catalyst to which the metal was added at Si/M=100 was determined by ICP analysis, and the metal content of the structured catalyst in which the metal was added at Si/M=50 and less than 100 was calculated based on XRF measurement results and ICP measurement results.

As a result, it was confirmed that the amount of the metal embedded in the structured catalyst increased as the added amount of the metal-containing solution increased, at least within a range that the ratio of numbers of atom was within from 50 to 1000.

[D] Performance Evaluation

The catalytic capacity (performance) of the solid acid nanoparticles was evaluated for the catalytic structural bodies and silicalite of the examples and comparative examples. The results are shown in Tables 1 to 6.

(1) Catalytic Activity

The catalytic activity was evaluated under the following conditions:

First, 0.4 g of the structured catalyst was charged in a normal pressure flow reactor, the total flow rate of the mixed gas of methanol gas and nitrogen (methanol concentration: 12.5%) was set to 222 ml, and (catalyst amount W)/(gas flow rate F) was adjusted to 0.67 g-cat h/mol, and a methanol reforming reaction was performed at 773 K.

After completion of the reaction, the generated gas and the generated liquid that were collected were analyzed by gas chromatography mass spectrometry (GC/MS) for the composition. Note that, as the analysis device for the generated gas, TRACE 1310 GC (available from Thermo Fisher Scientific Inc., detector: thermal conductivity detector) was used, and as the analysis device for the generated liquid, TRACE DSQ (available from Thermo Fisher Scientific Inc., detector: mass detector, ionization method: EI (ion source temperature 250° C., MS transfer line temperature of 320° C., detector: thermal conductivity detector)) was used.

Furthermore, based on the above analysis results, the yield (mol %) of the C2 to C4 olefins (for example, ethylene and propylene) was determined. The yield of the C2-C4 olefins was calculated as the percentage (mol %) of the total amount (mol) of the C2-C4 olefins contained in the production liquid (mol %) relative to the amount of methanol (mol) before the reaction.

In the present example, when the yield of the C2-C4 olefins contained in the product liquid was 30 mol % or more, the catalytic activity (resolution) was evaluated to be excellent, "A", when the yield was 20 mol % or more and less than 30 mol %, the catalytic activity was evaluated to be good, "B", when the yield was 10 mol % or more and less than 20 mol %, the catalytic activity was evaluated to be not good but at a pass level (acceptable), "C", and when the yield was less than 10 mol %, the catalytic activity was evaluated to be poor (unacceptable), "D".

(2) Durability (Life Time)

The durability was evaluated under the following conditions:

The structured catalyst was heated at 650° C. for 12 hours to produce a structured catalyst after heating. Next, using the obtained structured catalyst after heating, a reforming reaction of methanol gas was performed, and the components of the generated gas and the generated liquid were analyzed in the similar manner as in the above evaluation (1).

Based on the obtained analytical results, the yield (mol %) of C2-C4 olefins (mol %) was determined in the similar manner as in evaluation (1) above.

In the present example, when the yield of the C2-C4 olefins contained in the product liquid was maintained at 80 mol % or more, the durability (heat resistance) was evaluated to be excellent, "A", when the yield was maintained 60 mol % or more and less than 80 mol %, the durability (heat resistance) was evaluated to be good, "B", when the yield was maintained 40 mol % or more and less than 60 mol %, the durability (heat resistance) was evaluated to be not good but at a pass level (acceptable), "C", and when the yield was maintained at less than 40 mol %, the durability (heat resistance) was evaluated to be poor (unacceptable), "D".

Comparative Examples 1 to 3 were also subjected to the same performance evaluations as those in evaluations (1) and (2) above. Comparative Example 2 is the support itself and includes no catalytic substance. Therefore, in the performance evaluation described above, only the support of Comparative Example 2 was charged in place of the structured catalyst. The results are shown in Table 6.

The applicability of the structured catalyst to fluid catalytic cracking (FCC), a key process for petroleum refining, was also confirmed by the following evaluation.

0.2 g of the structured catalyst was charged into a normal pressure flow reactor, and a decomposition reaction of hexane (a model material) was performed at 650° C. for 1 hour. After completion of the reaction, the generated gas and the generated liquid that were collected were analyzed by gas chromatography mass spectrometry (GC/MS) for the composition. Note that, as the analysis device for the generated gas, TRACE 1310GC (available from Thermo Fisher Scientific Inc., detector: thermal conductivity detector) was used, and as the analysis device for the generated liquid, TRACE DSQ (available from Thermo Fisher Scientific Inc., detector: mass detector, ionization method: EI (ion source temperature 250° C., MS transfer line temperature of 320° C., detector: thermal conductivity detector)) was used.

Based on the results of the above-mentioned component analysis, the yield (mol %) of a compound having a molecular weight smaller than that of hexane (C5 or less hydrocarbon) was determined, and when the yield was 10 mol % or more, the catalytic activity (resolution) was evaluated to be excellent, "B", when the yield was 5 mol % or more and less than 10 mol %, the catalytic activity was evaluated to be good, "C", and when the yield was less than 5 mol %, the catalytic activity was evaluated to be poor (unacceptable), "D".

TABLE 1

| | Producing Conditions of Structured Catalyst | | | | | | |
|---|---|---|---|---|---|---|---|
| | Precursor Material (A) | | Addition to Precursor Material (A) | | Hydrothermal Treatment Conditions using Precursor Material (C) | | |
| | | | | Conversion Ratio (Ratio of Mass) of | Type of | | |
| No. | Type | Pore Diameter (nm) | Presence or Absence of Additives | Added Amount of Metal-containing Solution Si/M | Structure Directing Agent | pH | Time (h) |
| Example 1 | MCM-41 | 1.3 | Yes | 1000 | TEABr | 12 | 120 |
| Example 2 | | | | 500 | | | |
| Example 3 | | | | 200 | | | |
| Example 4 | | | | 100 | | | |

TABLE 1-continued

| No. | Framework | | Type | | | |
|---|---|---|---|---|---|---|
| Example 5 | | 2.0 | | | | |
| Example 6 | | 2.4 | | | | |
| Example 7 | | 2.6 | | | | |
| Example 8 | | 3.3 | | | | |
| Example 9 | | 6.6 | | | | |
| Example 10 | SBA-1 | 13.2 | | | | |
| Example 11 | | 19.8 | | | | |
| Example 12 | | 26.4 | | | | |
| Example 13 | MCM-41 | 1.3 | None | 1000 | | |
| Example 14 | | | | 500 | | |
| Example 15 | | | | 200 | | |
| Example 16 | | | | 100 | | |
| Example 17 | | 2.0 | | | | |
| Example 18 | | 2.4 | | | | |
| Example 19 | | 2.6 | | | | |
| Example 20 | | 3.3 | | | | |
| Example 21 | | 6.6 | | | | |
| Example 22 | SBA-1 | 13.2 | | | | |
| Example 23 | | 19.8 | | | | |
| Example 24 | | 26.4 | | | | |
| Example 25 | MCM-41 | 1.1 | Yes | 1000 | 11 | 72 |
| Example 26 | | | | 500 | | |
| Example 27 | | | | 200 | | |
| Example 28 | | | | 100 | | |
| Example 29 | | 1.6 | | | | |
| Example 30 | | 2.0 | | | | |
| Example 31 | | 2.2 | | | | |
| Example 32 | | 2.7 | | | | |
| Example 33 | | 5.4 | | | | |
| Example 34 | SBA-1 | 10.9 | | | | |
| Example 35 | | 16.3 | | | | |
| Example 36 | | 21.8 | | | | |
| Example 37 | MCM-41 | 1.1 | None | 1000 | | |
| Example 38 | | | | 500 | | |
| Example 39 | | | | 200 | | |
| Example 40 | | | | 100 | | |
| Example 41 | | 1.6 | | | | |
| Example 42 | | 2.0 | | | | |
| Example 43 | | 2.2 | | | | |
| Example 44 | | 2.7 | | | | |
| Example 45 | | 5.4 | | | | |
| Example 46 | SBA-1 | 10.9 | | | | |
| Example 47 | | 16.3 | | | | |
| Example 48 | | 21.8 | | | | |

| | Structured Catalyst | | | | | |
|---|---|---|---|---|---|---|
| | Support Zeolite-Type Compound | | Catalytic Substance | | | |
| | Average Inner Diameter of Channels | | Solid Acid Nanoparticles | | Performance Evaluation | |
| No. | Framework | $D_F$ (nm) | Type | Average Particle Size $D_C$ (nm) | $D_C/D_F$ | Catalytic Activity | Durability |
| Example 1 | FAU | 0.74 | $ZnO_x$ | 0.13 | 0.2 | C | C |
| Example 2 | | | | 0.40 | 0.5 | C | C |
| Example 3 | | | | 0.66 | 0.9 | B | C |
| Example 4 | | | | 1.32 | 1.8 | A | B |
| Example 5 | | | | 1.98 | 2.7 | A | B |
| Example 6 | | | | 2.38 | 3.2 | A | A |
| Example 7 | | | | 2.64 | 3.6 | A | A |
| Example 8 | | | | 3.30 | 4.5 | A | A |
| Example 9 | | | | 6.61 | 8.9 | B | A |
| Example 10 | | | | 13.21 | 17.9 | B | A |
| Example 11 | | | | 19.82 | 26.8 | C | A |
| Example 12 | | | | 26.43 | 35.7 | C | A |
| Example 13 | | | | 0.13 | 0.2 | C | C |
| Example 14 | | | | 0.40 | 0.5 | C | C |
| Example 15 | | | | 0.66 | 0.9 | B | C |
| Example 16 | | | | 1.32 | 1.8 | A | B |
| Example 17 | | | | 1.98 | 2.7 | A | B |
| Example 18 | | | | 2.38 | 3.2 | B | A |
| Example 19 | | | | 2.64 | 3.6 | B | A |
| Example 20 | | | | 3.30 | 4.5 | B | A |

TABLE 1-continued

| | | | | | | |
|---|---|---|---|---|---|---|
| Example 21 | | | 6.61 | 8.9 | C | A |
| Example 22 | | | 13.21 | 17.9 | C | A |
| Example 23 | | | 19.82 | 26.8 | C | A |
| Example 24 | | | 26.43 | 35.7 | C | A |
| Example 25 | MTW | 0.61 | 0.11 | 0.2 | C | C |
| Example 26 | | | 0.33 | 0.5 | C | C |
| Example 27 | | | 0.54 | 0.9 | B | C |
| Example 28 | | | 1.09 | 1.8 | A | B |
| Example 29 | | | 1.63 | 2.7 | A | B |
| Example 30 | | | 1.96 | 3.2 | A | B |
| Example 31 | | | 2.18 | 3.6 | A | A |
| Example 32 | | | 2.72 | 4.5 | A | A |
| Example 33 | | | 5.45 | 8.9 | B | A |
| Example 34 | | | 10.89 | 17.9 | B | A |
| Example 35 | | | 16.34 | 26.8 | C | A |
| Example 36 | | | 21.79 | 35.7 | C | A |
| Example 37 | | | 0.11 | 0.2 | C | C |
| Example 38 | | | 0.33 | 0.5 | C | C |
| Example 39 | | | 0.54 | 0.9 | B | C |
| Example 40 | | | 1.09 | 1.8 | A | B |
| Example 41 | | | 1.63 | 2.7 | A | B |
| Example 42 | | | 1.96 | 3.2 | A | B |
| Example 43 | | | 2.18 | 3.6 | B | A |
| Example 44 | | | 2.72 | 4.5 | B | A |
| Example 45 | | | 5.45 | 8.9 | C | A |
| Example 46 | | | 10.89 | 17.9 | C | A |
| Example 47 | | | 16.34 | 26.8 | C | A |
| Example 48 | | | 21.79 | 35.7 | C | A |

TABLE 2

| | Producing Conditions of Structured Catalyst | | | | | | |
|---|---|---|---|---|---|---|---|
| | Precursor Material (A) | | Addition to Precursor Material (A) | Conversion Ratio (Ratio of Mass) of Added Amount of Metal-containing Solution Si/M | Hydrothermal Treatment Conditions using Precursor Material (C) | | |
| No. | Type | Pore Diameter (nm) | Presence or Absence of Additives | | Type of Structure Directing Agent | pH | Time (h) |
| Example 49 | MCM-41 | 1.0 | Yes | 1000 | TPABr | 12 | 72 |
| Example 50 | | | | 500 | | | |
| Example 51 | | | | 200 | | | |
| Example 52 | | | | 100 | | | |
| Example 53 | | 1.5 | | | | | |
| Example 54 | | 1.8 | | | | | |
| Example 55 | | 2.0 | | | | | |
| Example 56 | | 2.5 | | | | | |
| Example 57 | | 5.0 | | | | | |
| Example 58 | SBA-1 | 10.0 | | | | | |
| Example 59 | | 15.0 | | | | | |
| Example 60 | | 20.0 | | | | | |
| Example 61 | MCM-41 | 1.0 | None | 1000 | | | |
| Example 62 | | | | 500 | | | |
| Example 63 | | | | 200 | | | |
| Example 64 | | | | 100 | | | |
| Example 65 | | 1.5 | | | | | |
| Example 66 | | 1.8 | | | | | |
| Example 67 | | 2.0 | | | | | |
| Example 68 | | 2.5 | | | | | |
| Example 69 | | 5.0 | | | | | |
| Example 70 | SBA-1 | 10.0 | | | | | |
| Example 71 | | 15.0 | | | | | |
| Example 72 | | 20.0 | | | | | |
| Example 73 | MCM-41 | 1.0 | Yes | 1000 | TMABr | 12 | 120 |
| Example 74 | | | | 500 | | | |
| Example 75 | | | | 200 | | | |
| Example 76 | | | | 100 | | | |
| Example 77 | | 1.5 | | | | | |
| Example 78 | | 1.8 | | | | | |

TABLE 2-continued

| | | | | | |
|---|---|---|---|---|---|
| Example 79 | | 2.0 | | | |
| Example 80 | | 2.5 | | | |
| Example 81 | | 5.1 | | | |
| Example 82 | SBA-1 | 10.2 | | | |
| Example 83 | | 15.3 | | | |
| Example 84 | | 20.4 | | | |
| Example 85 | MCM-41 | 1.0 | None | 1000 | |
| Example 86 | | | | 500 | |
| Example 87 | | | | 200 | |
| Example 88 | | | | 100 | |
| Example 89 | | 1.5 | | | |
| Example 90 | | 1.8 | | | |
| Example 91 | | 2.0 | | | |
| Example 92 | | 2.5 | | | |
| Example 93 | | 5.1 | | | |
| Example 94 | SBA-1 | 10.2 | | | |
| Example 95 | | 15.3 | | | |
| Example 96 | | 20.4 | | | |

| | Structured Catalyst | | | | | |
|---|---|---|---|---|---|---|
| | Support Zeolite-Type Compound | | Catalytic Substance Solid Acid Nanoparticles | | | |
| | Average Inner Diameter of Channels | | | Average Particle Size $D_C$ | Performance Evaluation | |
| No. | Framework | $D_F$ (nm) | Type | (nm) | $D_C/D_F$ | Catalytic Activity | Durability |
|---|---|---|---|---|---|---|---|
| Example 49 | MFI | 0.56 | $ZnO_x$ | 0.10 | 0.2 | C | C |
| Example 50 | | | | 0.30 | 0.5 | C | C |
| Example 51 | | | | 0.50 | 0.9 | B | C |
| Example 52 | | | | 1.00 | 1.8 | A | B |
| Example 53 | | | | 1.50 | 2.7 | A | B |
| Example 54 | | | | 1.80 | 3.2 | A | A |
| Example 55 | | | | 2.00 | 3.6 | A | A |
| Example 56 | | | | 2.50 | 4.5 | A | A |
| Example 57 | | | | 5.00 | 8.9 | B | A |
| Example 58 | | | | 10.00 | 17.9 | B | A |
| Example 59 | | | | 15.00 | 26.8 | C | A |
| Example 60 | | | | 20.00 | 35.7 | C | A |
| Example 61 | | | | 0.10 | 0.2 | C | C |
| Example 62 | | | | 0.30 | 0.5 | C | C |
| Example 63 | | | | 0.50 | 0.9 | B | C |
| Example 64 | | | | 1.00 | 1.8 | A | B |
| Example 65 | | | | 1.50 | 2.7 | A | B |
| Example 66 | | | | 1.80 | 3.2 | B | A |
| Example 67 | | | | 2.00 | 3.6 | B | A |
| Example 68 | | | | 2.50 | 4.5 | B | A |
| Example 69 | | | | 5.00 | 8.9 | C | A |
| Example 70 | | | | 10.00 | 17.9 | C | A |
| Example 71 | | | | 15.00 | 26.8 | C | A |
| Example 72 | | | | 20.00 | 35.7 | C | A |
| Example 73 | FER | 0.57 | | 0.10 | 0.2 | C | C |
| Example 74 | | | | 0.31 | 0.5 | C | C |
| Example 75 | | | | 0.51 | 0.9 | B | C |
| Example 76 | | | | 1.02 | 1.8 | A | B |
| Example 77 | | | | 1.53 | 2.7 | A | B |
| Example 78 | | | | 1.83 | 3.2 | A | B |
| Example 79 | | | | 2.04 | 3.6 | A | A |
| Example 80 | | | | 2.54 | 4.5 | A | A |
| Example 81 | | | | 5.09 | 8.9 | B | A |
| Example 82 | | | | 10.18 | 17.9 | B | A |
| Example 83 | | | | 15.27 | 26.8 | C | A |
| Example 84 | | | | 20.36 | 35.7 | C | A |
| Example 85 | | | | 0.10 | 0.2 | C | C |
| Example 86 | | | | 0.31 | 0.5 | C | C |
| Example 87 | | | | 0.51 | 0.9 | B | C |
| Example 88 | | | | 1.02 | 1.8 | A | B |
| Example 89 | | | | 1.53 | 2.7 | A | B |
| Example 90 | | | | 1.83 | 3.2 | A | B |
| Example 91 | | | | 2.04 | 3.6 | B | A |
| Example 92 | | | | 2.54 | 4.5 | B | A |
| Example 93 | | | | 5.09 | 8.9 | C | A |

TABLE 2-continued

| | | | | |
|---|---|---|---|---|
| Example 94 | 10.18 | 17.9 | C | A |
| Example 95 | 15.27 | 26.8 | C | A |
| Example 96 | 20.36 | 35.7 | C | A |

TABLE 3

| | Producing Conditions of Structured Catalyst | | | | | | |
|---|---|---|---|---|---|---|---|
| | Precursor Material (A) | | Addition to Precursor Material (A) | | | Hydrothermal Treatment Conditions using Precursor Material (C) | |
| No. | Type | Pore Diameter (nm) | Presence or Absence of Additives | Conversion Ratio (Ratio of Mass) of Added Amount of Metal-containing Solution Si/M | Type of Structure Directing Agent | pH | Time (h) |
| Example 97 | MCM-41 | 1.3 | Yes | 1000 | TEABr | 12 | 120 |
| Example 98 | | | | 500 | | | |
| Example 99 | | | | 200 | | | |
| Example 100 | | | | 100 | | | |
| Example 101 | | 2.0 | | | | | |
| Example 102 | | 2.4 | | | | | |
| Example 103 | | 2.6 | | | | | |
| Example 104 | | 3.3 | | | | | |
| Example 105 | | 6.6 | | | | | |
| Example 106 | SBA-1 | 13.2 | | | | | |
| Example 107 | | 19.8 | | | | | |
| Example 108 | | 26.4 | | | | | |
| Example 109 | MCM-41 | 1.3 | None | 1000 | | | |
| Example 110 | | | | 500 | | | |
| Example 111 | | | | 200 | | | |
| Example 112 | | | | 100 | | | |
| Example 113 | | 2.0 | | | | | |
| Example 114 | | 2.4 | | | | | |
| Example 115 | | 2.6 | | | | | |
| Example 116 | | 3.3 | | | | | |
| Example 117 | | 6.6 | | | | | |
| Example 118 | SBA-1 | 13.2 | | | | | |
| Example 119 | | 19.8 | | | | | |
| Example 120 | | 26.4 | | | | | |
| Example 121 | MCM-41 | 1.1 | Yes | 1000 | | 11 | 72 |
| Example 122 | | | | 500 | | | |
| Example 123 | | | | 200 | | | |
| Example 124 | | | | 100 | | | |
| Example 125 | | 1.6 | | | | | |
| Example 126 | | 2.0 | | | | | |
| Example 127 | | 2.2 | | | | | |
| Example 128 | | 2.7 | | | | | |
| Example 129 | | 5.4 | | | | | |
| Example 130 | SBA-1 | 10.9 | | | | | |
| Example 131 | | 16.3 | | | | | |
| Example 132 | | 21.8 | | | | | |
| Example 133 | MCM-41 | 1.1 | None | 1000 | | | |
| Example 134 | | | | 500 | | | |
| Example 135 | | | | 200 | | | |
| Example 136 | | | | 100 | | | |
| Example 137 | | 1.6 | | | | | |
| Example 138 | | 2.0 | | | | | |
| Example 139 | | 2.2 | | | | | |
| Example 140 | | 2.7 | | | | | |
| Example 141 | | 5.4 | | | | | |
| Example 142 | SBA-1 | 10.9 | | | | | |
| Example 143 | | 16.3 | | | | | |
| Example 144 | | 21.8 | | | | | |

TABLE 3-continued

| No. | Structured Catalyst Support Zeolite-Type Compound Framework | Average Inner Diameter of Channels $D_F$ (nm) | Catalytic Substance Solid Acid Nanoparticles Type | Average Particle Size $D_C$ (nm) | $D_C/D_F$ | Performance Evaluation Catalytic Activity | Durability |
|---|---|---|---|---|---|---|---|
| Example 97 | FAU | 0.74 | AlO$_x$ | 0.13 | 0.2 | C | C |
| Example 98 | | | | 0.40 | 0.5 | C | C |
| Example 99 | | | | 0.66 | 0.9 | B | C |
| Example 100 | | | | 1.32 | 1.8 | A | B |
| Example 101 | | | | 1.98 | 2.7 | A | B |
| Example 102 | | | | 2.38 | 3.2 | A | A |
| Example 103 | | | | 2.64 | 3.6 | A | A |
| Example 104 | | | | 3.30 | 4.5 | A | A |
| Example 105 | | | | 6.61 | 8.9 | B | A |
| Example 106 | | | | 13.21 | 17.9 | B | A |
| Example 107 | | | | 19.82 | 26.8 | C | A |
| Example 108 | | | | 26.43 | 35.7 | C | A |
| Example 109 | | | | 0.13 | 0.2 | C | C |
| Example 110 | | | | 0.40 | 0.5 | C | C |
| Example 111 | | | | 0.66 | 0.9 | B | C |
| Example 112 | | | | 1.32 | 1.8 | A | B |
| Example 113 | | | | 1.98 | 2.7 | A | B |
| Example 114 | | | | 2.38 | 3.2 | B | A |
| Example 115 | | | | 2.64 | 3.6 | B | A |
| Example 116 | | | | 3.30 | 4.5 | B | A |
| Example 117 | | | | 6.61 | 8.9 | C | A |
| Example 118 | | | | 13.21 | 17.9 | C | A |
| Example 119 | | | | 19.82 | 26.8 | C | A |
| Example 120 | | | | 26.43 | 35.7 | C | A |
| Example 121 | MTW | 0.61 | | 0.11 | 0.2 | C | C |
| Example 122 | | | | 0.33 | 0.5 | C | C |
| Example 123 | | | | 0.54 | 0.9 | B | C |
| Example 124 | | | | 1.09 | 1.8 | A | B |
| Example 125 | | | | 1.63 | 2.7 | A | B |
| Example 126 | | | | 1.96 | 3.2 | A | B |
| Example 127 | | | | 2.18 | 3.6 | A | A |
| Example 128 | | | | 2.72 | 4.5 | A | A |
| Example 129 | | | | 5.45 | 8.9 | B | A |
| Example 130 | | | | 10.89 | 17.9 | B | A |
| Example 131 | | | | 16.34 | 26.8 | C | A |
| Example 132 | | | | 21.79 | 35.7 | C | A |
| Example 133 | | | | 0.11 | 0.2 | C | C |
| Example 134 | | | | 0.33 | 0.5 | C | C |
| Example 135 | | | | 0.54 | 0.9 | B | C |
| Example 136 | | | | 1.09 | 1.8 | A | B |
| Example 137 | | | | 1.63 | 2.7 | A | B |
| Example 138 | | | | 1.96 | 3.2 | A | B |
| Example 139 | | | | 2.18 | 3.6 | B | A |
| Example 140 | | | | 2.72 | 4.5 | B | A |
| Example 141 | | | | 5.45 | 8.9 | C | A |
| Example 142 | | | | 10.89 | 17.9 | C | A |
| Example 143 | | | | 16.34 | 26.8 | C | A |
| Example 144 | | | | 21.79 | 35.7 | C | A |

TABLE 4

| | Producing Conditions of Structured Catalyst | | | | | | |
|---|---|---|---|---|---|---|---|
| | Precursor Material (A) | | Addition to Precursor Material (A) | Conversion Ratio (Ratio of Mass) of | Hydrothermal Treatment Conditions using Precursor Material (C) | | |
| No. | Type | Pore Diameter (nm) | Presence or Absence of Additives | Added Amount of Metal-containing Solution Si/M | Type of Structure Directing Agent | pH | Time (h) |
| Example 145 | MCM-41 | 1.0 | Yes | 1000 | TPABr | 12 | 72 |
| Example 146 | | | | 500 | | | |
| Example 147 | | | | 200 | | | |
| Example 148 | | | | 100 | | | |
| Example 149 | | 1.5 | | | | | |
| Example 150 | | 1.8 | | | | | |
| Example 151 | | 2.0 | | | | | |
| Example 152 | | 2.5 | | | | | |
| Example 153 | | 5.0 | | | | | |
| Example 154 | SBA-1 | 10.0 | | | | | |
| Example 155 | | 15.0 | | | | | |
| Example 156 | | 20.0 | | | | | |
| Example 157 | MCM-41 | 1.0 | None | 1000 | | | |
| Example 158 | | | | 500 | | | |
| Example 159 | | | | 200 | | | |
| Example 160 | | | | 100 | | | |
| Example 161 | | 1.5 | | | | | |
| Example 162 | | 1.8 | | | | | |
| Example 163 | | 2.0 | | | | | |
| Example 164 | | 2.5 | | | | | |
| Example 165 | | 5.0 | | | | | |
| Example 166 | SBA-1 | 10.0 | | | | | |
| Example 167 | | 15.0 | | | | | |
| Example 168 | | 20.0 | | | | | |
| Example 169 | MCM-41 | 1.0 | Yes | 1000 | TMABr | 12 | 120 |
| Example 170 | | | | 500 | | | |
| Example 171 | | | | 200 | | | |
| Example 172 | | | | 100 | | | |
| Example 173 | | 1.5 | | | | | |
| Example 174 | | 1.8 | | | | | |
| Example 175 | | 2.0 | | | | | |
| Example 176 | | 2.5 | | | | | |
| Example 177 | | 5.1 | | | | | |
| Example 178 | SBA-1 | 10.2 | | | | | |
| Example 179 | | 15.3 | | | | | |
| Example 180 | | 20.4 | | | | | |
| Example 181 | MCM-41 | 1.0 | None | 1000 | | | |
| Example 182 | | | | 500 | | | |
| Example 183 | | | | 200 | | | |
| Example 184 | | | | 100 | | | |
| Example 185 | | 1.5 | | | | | |
| Example 186 | | 1.8 | | | | | |
| Example 187 | | 2.0 | | | | | |
| Example 188 | | 2.5 | | | | | |
| Example 189 | | 5.1 | | | | | |
| Example 190 | SBA-1 | 10.2 | | | | | |
| Example 191 | | 15.0 | | | | | |
| Example 192 | | 20.0 | | | | | |

| | Structured Catalyst | | | | | | |
|---|---|---|---|---|---|---|---|
| | Support Zeolite-Type Compound | | Catalytic Substance Solid Acid Nanoparticles | | | Performance Evaluation | |
| No. | Framework | Average Inner Diameter of Channels $D_F$ (nm) | Type | Average Particle Size $D_C$ (nm) | $D_C/D_F$ | Catalytic Activity | Durability |
| Example 145 | MFI | 0.56 | $AlO_x$ | 0.10 | 0.2 | C | C |
| Example 146 | | | | 0.30 | 0.5 | C | C |
| Example 147 | | | | 0.50 | 0.9 | B | C |

TABLE 4-continued

| | | | | | | |
|---|---|---|---|---|---|---|
| Example 148 | | | 1.00 | 1.8 | A | B |
| Example 149 | | | 1.50 | 2.7 | A | B |
| Example 150 | | | 1.80 | 3.2 | A | A |
| Example 151 | | | 2.00 | 3.6 | A | A |
| Example 152 | | | 2.50 | 4.5 | A | A |
| Example 153 | | | 5.00 | 8.9 | B | A |
| Example 154 | | | 10.00 | 17.9 | B | A |
| Example 155 | | | 15.00 | 26.8 | C | A |
| Example 156 | | | 20.00 | 35.7 | C | A |
| Example 157 | | | 0.10 | 0.2 | C | C |
| Example 158 | | | 0.30 | 0.5 | C | C |
| Example 159 | | | 0.50 | 0.9 | B | C |
| Example 160 | | | 1.00 | 1.8 | A | B |
| Example 161 | | | 1.50 | 2.7 | A | B |
| Example 162 | | | 1.80 | 3.2 | B | A |
| Example 163 | | | 2.00 | 3.6 | B | A |
| Example 164 | | | 2.50 | 4.5 | B | A |
| Example 165 | | | 5.00 | 8.9 | C | A |
| Example 166 | | | 10.00 | 17.9 | C | A |
| Example 167 | | | 15.00 | 26.8 | C | A |
| Example 168 | | | 20.00 | 35.7 | C | A |
| Example 169 | FER | 0.57 | 0.10 | 0.2 | C | C |
| Example 170 | | | 0.31 | 0.5 | C | C |
| Example 171 | | | 0.51 | 0.9 | B | C |
| Example 172 | | | 1.02 | 1.8 | A | B |
| Example 173 | | | 1.53 | 2.7 | A | B |
| Example 174 | | | 1.83 | 3.2 | A | B |
| Example 175 | | | 2.04 | 3.6 | A | A |
| Example 176 | | | 2.54 | 4.5 | A | A |
| Example 177 | | | 5.09 | 8.9 | B | A |
| Example 178 | | | 10.18 | 17.9 | B | A |
| Example 179 | | | 15.27 | 26.8 | C | A |
| Example 180 | | | 20.36 | 35.7 | C | A |
| Example 181 | | | 0.10 | 0.2 | C | C |
| Example 182 | | | 0.31 | 0.5 | C | C |
| Example 183 | | | 0.51 | 0.9 | B | C |
| Example 184 | | | 1.02 | 1.8 | A | B |
| Example 185 | | | 1.53 | 2.7 | A | B |
| Example 186 | | | 1.83 | 3.2 | A | B |
| Example 187 | | | 2.04 | 3.6 | B | A |
| Example 188 | | | 2.54 | 4.5 | B | A |
| Example 189 | | | 5.09 | 8.9 | C | A |
| Example 190 | | | 10.18 | 17.9 | C | A |
| Example 191 | | 0.56 | 15.00 | 26.8 | C | A |
| Example 192 | | | 20.00 | 35.7 | C | A |

TABLE 5

| | Producing Conditions of Structured Catalyst | | | | | | |
|---|---|---|---|---|---|---|---|
| | Precursor Material (A) | | | Addition to Precursor Material (A) Conversion Ratio (Ratio of Mass) of Added Amount of Metal-containing Solution Si/M | Hydrothermal Treatment Conditions using Precursor Material (C) | | |
| No. | Type | Pore Diameter (nm) | Presence or Absence of Additives | | Type of Structure Directing Agent | pH | Time (h) |
| Example 193 | MCM-41 | 1.3 | Yes | 1000 | TEABr | 12 | 120 |
| Example 194 | | | | 500 | | | |
| Example 195 | | | | 200 | | | |
| Example 196 | | | | 100 | | | |
| Example 197 | | 2.0 | | | | | |
| Example 198 | | 2.4 | | | | | |
| Example 199 | | 2.6 | | | | | |
| Example 200 | | 3.3 | | | | | |
| Example 201 | | 6.6 | | | | | |
| Example 202 | SBA-1 | 13.2 | | | | | |
| Example 203 | | 19.8 | | | | | |
| Example 204 | | 26.4 | | | | | |
| Example 205 | MCM-41 | 1.3 | None | 1000 | | | |
| Example 206 | | | | 500 | | | |

TABLE 5-continued

| No. | Framework | | | | | | |
|---|---|---|---|---|---|---|---|
| Example 207 | | | | 200 | | | |
| Example 208 | | | | 100 | | | |
| Example 209 | | 2.0 | | | | | |
| Example 210 | | 2.4 | | | | | |
| Example 211 | | 2.6 | | | | | |
| Example 212 | | 3.3 | | | | | |
| Example 213 | | 6.6 | | | | | |
| Example 214 | SBA-1 | 13.2 | | | | | |
| Example 215 | | 19.8 | | | | | |
| Example 216 | | 26.4 | | | | | |
| Example 217 | MCM-41 | 1.1 | Yes | 1000 | | 11 | 72 |
| Example 218 | | | | 500 | | | |
| Example 219 | | | | 200 | | | |
| Example 220 | | | | 100 | | | |
| Example 221 | | 1.6 | | | | | |
| Example 222 | | 2.0 | | | | | |
| Example 223 | | 2.2 | | | | | |
| Example 224 | | 2.7 | | | | | |
| Example 225 | | 5.4 | | | | | |
| Example 226 | SBA-1 | 10.9 | | | | | |
| Example 227 | | 16.3 | | | | | |
| Example 228 | | 21.8 | | | | | |
| Example 229 | MCM-41 | 1.1 | None | 1000 | | | |
| Example 230 | | | | 500 | | | |
| Example 231 | | | | 200 | | | |
| Example 232 | | | | 100 | | | |
| Example 233 | | 1.6 | | | | | |
| Example 234 | | 2.0 | | | | | |
| Example 235 | | 2.2 | | | | | |
| Example 236 | | 2.7 | | | | | |
| Example 237 | | 5.4 | | | | | |
| Example 238 | SBA-1 | 10.9 | | | | | |
| Example 239 | | 16.3 | | | | | |
| Example 240 | | 21.8 | | | | | |

| | Structured Catalyst | | | | | |
|---|---|---|---|---|---|---|
| | Support Zeolite-Type Compound | | Catalytic Substance Solid Acid Nanoparticles | | | Performance Evaluation | |
| No. | Framework | Average Inner Diameter of Channels $D_F$ (nm) | Type | Average Particle Size $D_C$ (nm) | $D_C/D_F$ | Catalytic Activity | Durability |
| Example 193 | FAU | 0.74 | $ZrO_x$ | 0.13 | 0.2 | C | C |
| Example 194 | | | | 0.40 | 0.5 | C | C |
| Example 195 | | | | 0.66 | 0.9 | B | C |
| Example 196 | | | | 1.32 | 1.8 | A | B |
| Example 197 | | | | 1.98 | 2.7 | A | B |
| Example 198 | | | | 2.38 | 3.2 | A | A |
| Example 199 | | | | 2.64 | 3.6 | A | A |
| Example 200 | | | | 3.30 | 4.5 | A | A |
| Example 201 | | | | 6.61 | 8.9 | B | A |
| Example 202 | | | | 13.21 | 17.9 | B | A |
| Example 203 | | | | 19.82 | 26.8 | C | A |
| Example 204 | | | | 26.43 | 35.7 | C | A |
| Example 205 | | | | 0.13 | 0.2 | C | C |
| Example 206 | | | | 0.40 | 0.5 | C | C |
| Example 207 | | | | 0.66 | 0.9 | B | C |
| Example 208 | | | | 1.32 | 1.8 | A | B |
| Example 209 | | | | 1.98 | 2.7 | A | B |
| Example 210 | | | | 2.38 | 3.2 | B | A |
| Example 211 | | | | 2.64 | 3.6 | B | A |
| Example 212 | | | | 3.30 | 4.5 | B | A |
| Example 213 | | | | 6.61 | 8.9 | C | A |
| Example 214 | | | | 13.21 | 17.9 | C | A |
| Example 215 | | | | 19.82 | 26.8 | C | A |
| Example 216 | | | | 26.43 | 35.7 | C | A |
| Example 217 | MTW | 0.61 | | 0.11 | 0.2 | C | C |
| Example 218 | | | | 0.33 | 0.5 | C | C |
| Example 219 | | | | 0.54 | 0.9 | B | C |
| Example 220 | | | | 1.09 | 1.8 | A | B |
| Example 221 | | | | 1.63 | 2.7 | A | B |
| Example 222 | | | | 1.96 | 3.2 | A | B |
| Example 223 | | | | 2.18 | 3.6 | A | A |
| Example 224 | | | | 2.72 | 4.5 | A | A |

TABLE 5-continued

| | | | | | |
|---|---|---|---|---|---|
| Example 225 | | 5.45 | 8.9 | B | A |
| Example 226 | | 10.89 | 17.9 | B | A |
| Example 227 | | 16.34 | 26.8 | C | A |
| Example 228 | | 21.79 | 35.7 | C | A |
| Example 229 | | 0.11 | 0.2 | C | C |
| Example 230 | | 0.33 | 0.5 | C | C |
| Example 231 | | 0.54 | 0.9 | B | C |
| Example 232 | | 1.09 | 1.8 | A | B |
| Example 233 | | 1.63 | 2.7 | A | B |
| Example 234 | | 1.96 | 3.2 | A | B |
| Example 235 | | 2.18 | 3.6 | B | A |
| Example 236 | | 2.72 | 4.5 | B | A |
| Example 237 | | 5.45 | 8.9 | C | A |
| Example 238 | | 10.89 | 17.9 | C | A |
| Example 239 | | 16.34 | 26.8 | C | A |
| Example 240 | | 21.79 | 35.7 | C | A |

TABLE 6

| | Producing Conditions of Structured Catalyst | | | | | | |
|---|---|---|---|---|---|---|---|
| | Precursor Material (A) | | Addition to Precursor Material (A) | Conversion Ratio (Ratio of Mass) of | Hydrothermal Treatment Conditions using Precursor Material (C) | | |
| No. | Type | Pore Diameter (nm) | Presence or Absence of Additives | Added Amount of Metal-containing Solution Si/M | Type of Structure Directing Agent | pH | Time (h) |
| Example 241 | MCM-41 | 1.0 | Yes | 1000 | TPABr | 12 | 72 |
| Example 242 | | | | 500 | | | |
| Example 243 | | | | 200 | | | |
| Example 244 | | | | 100 | | | |
| Example 245 | | 1.5 | | | | | |
| Example 246 | | 1.8 | | | | | |
| Example 247 | | 2.0 | | | | | |
| Example 248 | | 2.5 | | | | | |
| Example 249 | | 5.0 | | | | | |
| Example 250 | SBA-1 | 10.0 | | | | | |
| Example 251 | | 15.0 | | | | | |
| Example 252 | | 20.0 | | | | | |
| Example 253 | MCM-41 | 1.0 | None | 1000 | | | |
| Example 254 | | | | 500 | | | |
| Example 255 | | | | 200 | | | |
| Example 256 | | | | 100 | | | |
| Example 257 | | 1.5 | | | | | |
| Example 258 | | 1.8 | | | | | |
| Example 259 | | 2.0 | | | | | |
| Example 260 | | 2.5 | | | | | |
| Example 261 | | 5.0 | | | | | |
| Example 262 | SBA-1 | 10.0 | | | | | |
| Example 263 | | 15.0 | | | | | |
| Example 264 | | 20.0 | | | | | |
| Example 265 | MCM-41 | 1.0 | Yes | 1000 | TMABr | 12 | 120 |
| Example 266 | | | | 500 | | | |
| Example 267 | | | | 200 | | | |
| Example 268 | | | | 100 | | | |
| Example 269 | | 1.5 | | | | | |
| Example 270 | | 1.8 | | | | | |
| Example 271 | | 2.0 | | | | | |
| Example 272 | | 2.5 | | | | | |
| Example 273 | | 5.1 | | | | | |
| Example 274 | SBA-1 | 10.2 | | | | | |
| Example 275 | | 15.3 | | | | | |
| Example 276 | | 20.4 | | | | | |
| Example 277 | MCM-41 | 1.0 | None | 1000 | | | |
| Example 278 | | | | 500 | | | |
| Example 279 | | | | 200 | | | |
| Example 280 | | | | 100 | | | |
| Example 281 | | 1.5 | | | | | |
| Example 282 | | 1.8 | | | | | |
| Example 283 | | 2.0 | | | | | |

TABLE 6-continued

| | | |
|---|---|---|
| Example 284 | | 2.5 |
| Example 285 | | 5.1 |
| Example 286 | SBA-1 | 10.2 |
| Example 287 | | 15.3 |
| Example 288 | | 20.4 |
| Comparative Example 1 | | — |
| Comparative Example 2 | | — |
| Comparative Example 3 | | — |

| | Structured Catalyst | | | | | |
|---|---|---|---|---|---|---|
| | Support Zeolite-Type Compound | | Catalytic Substance Solid Acid Nanoparticles | | | Performance Evaluation |
| No. | Framework | Average Inner Diameter of Channels $D_F$ (nm) | Type | Average Particle Size $D_C$ (nm) | $D_C/D_F$ | Catalytic Activity | Durability |
| Example 241 | MFI | 0.56 | ZrO$_x$ | 0.10 | 0.2 | C | C |
| Example 242 | | | | 0.30 | 0.5 | C | C |
| Example 243 | | | | 0.50 | 0.9 | B | C |
| Example 244 | | | | 1.00 | 1.8 | A | B |
| Example 245 | | | | 1.50 | 2.7 | A | B |
| Example 246 | | | | 1.80 | 3.2 | A | A |
| Example 247 | | | | 2.00 | 3.6 | A | A |
| Example 248 | | | | 2.50 | 4.5 | A | A |
| Example 249 | | | | 5.00 | 8.9 | B | A |
| Example 250 | | | | 10.00 | 17.9 | B | A |
| Example 251 | | | | 15.00 | 26.8 | C | A |
| Example 252 | | | | 25.00 | 44.6 | C | A |
| Example 253 | | | | 0.10 | 0.2 | C | C |
| Example 254 | | | | 0.30 | 0.5 | C | C |
| Example 255 | | | | 0.50 | 0.9 | B | C |
| Example 256 | | | | 1.00 | 1.8 | A | B |
| Example 257 | | | | 1.50 | 2.7 | A | B |
| Example 258 | | | | 1.80 | 3.2 | B | A |
| Example 259 | | | | 2.00 | 3.6 | B | A |
| Example 260 | | | | 2.50 | 4.5 | B | A |
| Example 261 | | | | 5.00 | 8.9 | C | A |
| Example 262 | | | | 10.00 | 17.9 | C | A |
| Example 263 | | | | 15.00 | 26.8 | C | A |
| Example 264 | | | | 20.00 | 35.7 | C | A |
| Example 265 | FER | 0.57 | | 0.10 | 0.2 | C | C |
| Example 266 | | | | 0.31 | 0.5 | C | C |
| Example 267 | | | | 0.51 | 0.9 | B | C |
| Example 268 | | | | 1.02 | 1.8 | A | B |
| Example 269 | | | | 1.53 | 2.7 | A | B |
| Example 270 | | | | 1.83 | 3.2 | A | B |
| Example 271 | | | | 2.04 | 3.6 | A | A |
| Example 272 | | | | 2.54 | 4.5 | A | A |
| Example 273 | | | | 5.09 | 8.9 | B | A |
| Example 274 | | | | 10.18 | 17.9 | B | A |
| Example 275 | | | | 15.27 | 26.8 | C | A |
| Example 276 | | | | 20.36 | 35.7 | C | A |
| Example 277 | | | | 0.10 | 0.2 | C | C |
| Example 278 | | | | 0.31 | 0.5 | C | C |
| Example 279 | | | | 0.51 | 0.9 | B | C |
| Example 280 | | | | 1.02 | 1.8 | A | B |
| Example 281 | | | | 1.53 | 2.7 | A | B |
| Example 282 | | | | 1.83 | 3.2 | A | B |
| Example 283 | | | | 2.04 | 3.6 | B | A |
| Example 284 | | | | 2.54 | 4.5 | B | A |
| Example 285 | | | | 5.09 | 8.9 | C | A |
| Example 286 | | | | 10.18 | 17.9 | C | A |
| Example 287 | | | | 15.27 | 26.8 | C | A |
| Example 288 | | | | 20.36 | 35.7 | C | A |
| Comparative Example 1 | MFI | 0.74 | CoO$_x$ | ≤50 | ≤67.6 | C | D |
| Comparative Example 2 | MFI | 0.61 | — | ≤50 | ≤82.0 | D | D |
| Comparative Example 3 | MFI | 0.56 | Al$_2$O$_3$ | ≤50 | ≤89.3 | D | D |

TABLE 7

| | Structured Catalyst | | | | | | | |
|---|---|---|---|---|---|---|---|---|
| | Support Zeolite-Type Compound | | Catalytic Substance Metal Nanoparticles | | | | | |
| | | Average Inner Diameter of Channels $D_F$ | | Average Particle Size $D_C$ | | Performance Evaluation | | |
| No. | Framework | (nm) | Type | (nm) | $D_C/D_F$ | Catalytic Activity | Durability | FCC Reaction |
| Example 102 | FAU | 0.74 | $AlO_x$ | 2.38 | 3.2 | A | A | B |
| Example 103 | | | | 2.64 | 3.6 | A | A | B |
| Example 104 | | | | 3.30 | 4.5 | A | A | B |
| Example 127 | MTW | 0.61 | | 2.18 | 3.6 | A | A | B |
| Example 128 | | | | 2.72 | 4.5 | A | A | B |
| Example 150 | MFI | 0.56 | | 1.8 | 3.2 | A | A | B |
| Example 151 | | 0.56 | | 2.0 | 3.6 | A | A | B |
| Example 152 | | 0.56 | | 2.5 | 4.5 | A | A | B |
| Example 175 | FER | 0.57 | | 2.0 | 3.6 | A | A | B |
| Example 176 | | 0.57 | | 2.5 | 4.5 | A | A | B |
| Example 289 | FAU | 0.74 | $FeO_x$ | 2.38 | 3.2 | A | A | C |
| Example 290 | | | | 2.64 | 3.6 | A | A | C |
| Example 291 | | | | 3.30 | 4.5 | A | A | C |
| Example 292 | MTW | 0.61 | | 2.18 | 3.6 | A | A | C |
| Example 293 | | | | 2.72 | 4.5 | A | A | C |
| Example 294 | MFI | 0.56 | | 1.80 | 3.2 | A | A | C |
| Example 295 | | 0.56 | | 2.00 | 3.6 | A | A | C |
| Example 296 | | 0.56 | | 2.50 | 4.5 | A | A | C |
| Example 297 | FER | 0.57 | | 2.04 | 3.6 | A | A | C |
| Example 298 | | 0.57 | | 2.54 | 4.5 | A | A | C |

As can be seen from Tables 1 to 7, the catalytic structural bodies (Examples 1 to 298), which was confirmed by cross-sectional observation to hold the catalytic substance in the support was found to exhibit excellent catalytic activity in the reforming reaction of methanol gas and excellent durability as a catalyst compared to the structured catalyst in which the catalytic substance was simply adhered to the outer surface of the support (Comparative Examples 1 and 3) or the support itself having no catalytic substance (Comparative Example 2). Furthermore, the analysis results indicate that aromatic hydrocarbons (e.g. benzene, xylene, and toluene) can also be produced.

On the other hand, the support of Comparative Example 2, which had no catalytic substances, exhibited little catalytic activity in the reforming reaction of methanol gas, and both the catalytic activity and the durability were inferior compared to the catalytic structural bodies of Examples 1 to 298.

In addition, in the catalytic structural bodies of Comparative Examples 1 and 3 in which the catalytic substance was attached only to the outer surface of the support, the catalytic activity in the reforming reaction of methanol gas was improved compared to the support itself of Comparative Example 2, which had no catalytic substances, but inferior durability as a catalyst was exhibited compared to the catalytic structural bodies of Examples 1 to 298.

Other Embodiments

A method for producing at least one of an olefin or an aromatic hydrocarbon from methanol using a catalyst, the catalyst including a support of a porous structure composed of a zeolite-type compound and at least one type of metal nanoparticles present in the support, the support having channels communicating with each other, and the metal nanoparticles including a structured catalyst held in at least an enlarged pore portion of the channels of the support.

A method for producing high octane gasoline together with propylene or the like by subjecting a high boiling point hydrocarbon such as alkylbenzene as a raw material to fluid catalytic cracking (FCC) treatment using a catalyst, the catalyst including a support of a porous structure composed of a zeolite-type compound and at least one type of metal nanoparticles present in the support, the support having channels communicating with each other, and the metal nanoparticles including a structured catalyst held in at least an enlarged pore portion of the channels of the support. As a result, high octane gasoline can be produced with propylene or the like, the catalyst suppresses aggregation of the catalytic substances and thus maintains catalytic activity over a longer period of time than prior art catalysts, and a long life of the catalyst can be achieved.

REFERENCE SIGNS LIST 1, 2 Catalytic structural bodies
10 Support
10a Outer surface
11 Channel
11a Pore
12 Enlarged pore portion
20 Solid acid
30 Catalytic substance

What is claimed is:
1. A structured catalyst for methanol reforming, comprising:
a support of a porous structure composed of a zeolite-type compound; and
a catalytic substance present in the support, wherein
the zeolite-type compound is selected from the group consisting of zeolites, cation exchanged zeolites and silicalites,
a framework of the zeolite-type compound is selected from the group consisting of EAU type (Y type or X type), MTW type, MFI type (ZSM-5), FER type (ferrierite), LTA type (A type), MWW type (MCM-22), MOR type (mordenite), LTL type (L type), and BEA type (beta type),
the support comprises channels connecting with each other,
the catalytic substance is a solid acid and is present at least in the channels of the support,
the solid acid is selected from the group consisting of iron oxide ($FeO_x$), zinc oxide (ZnO), aluminum oxide ($Al_2O_3$), zirconium oxide ($ZrO_2$), titanium oxide ($TiO_2$), selenium trioxide ($SeO_3$), selenium dioxide ($SeO_2$), tellurium trioxide ($TeO_3$), tellurium dioxide ($TeO_2$), tin dioxide ($SnO_2$), manganese oxide ($Mn_2O_7$), technetium oxide ($Tc_2O_7$), and rhenium oxide ($Re_2O_7$),
the channels comprise any one of a one-dimensional pore, a two-dimensional pore, and a three-dimensional pore defined by a framework of the zeolite-type compound and an enlarged pore portion that is greater than any one of the one-dimensional pore, the two-dimensional pore, and the three-dimensional pore and is not defined by the framework of the zeolite-type compound, wherein the enlarged pore portion is greater than or equal to a diameter of the catalytic substance,
a particle size of the catalytic substance is greater than an inner diameter of any one of the one-dimensional pore, the two-dimensional pore, and the three-dimensional pore,
the catalytic substance is at least embedded in the enlarged pore portion, and
the solid acid is nanoparticles.

2. The structured catalyst for methanol reforming according to claim 1, wherein the enlarged pore portion connects with a plurality of pores constituting any one of the one-dimensional pore, the two-dimensional pore, and the three-dimensional pore.

3. The structured catalyst fir methanol reforming according to claim 1, wherein an average particle size of the nanoparticles is greater than an average inner diameter of the channels and is less than or equal to an inner diameter of the enlarged pore portion.

4. The structured catalyst for methanol reforming according to claim 1, wherein an average particle size of the nanoparticles is from 0.1 nm to 50 nm.

5. The structured catalyst for methanol reforming according to claim 3, wherein a ratio of the average particle size of the nanoparticles to the average inner diameter of the channels is from 0.06 to 500.

6. The structured catalyst for methanol reforming according to claim 5, wherein the ratio of the average particle size of the nanoparticles to the average inner diameter of the channels is from 0.1 to 36.

7. The structured catalyst for methanol reforming according to claim 5, wherein the ratio of the average particle size of the nanoparticles to the average inner diameter of the channels is from 1.7 to 4.5.

8. The structured catalyst for methanol reforming according to claim 1, wherein a metal of the solid oxide nanoparticles is present in an amount of from 0.5 to 2.5 mass % relative to the structured catalyst for methanol reforming.

9. The structured catalyst for methanol reforming according to claim 1, wherein
an average inner diameter of the channels is from 0.1 nm to 1.5 nm, and
an inner diameter of the enlarged pore portion is from 0.5 nm to 50 nm.

10. The structured catalyst for methanol reforming according to claim 1, further comprising at least one other catalytic substance held on an outer surface of the support.

11. The structured catalyst for methanol reforming according to claim 10, wherein a content of the catalytic substance present in the support is greater than a content of the at least one other catalytic substance held on the outer surface of the support.

12. A methanol reforming device including the structured catalyst for methanol reforming described in claim 1.

13. The structured catalyst for methanol reforming according to claim 1, wherein the zeolite-type compound comprises a plurality of pores less than 1 nm in diameter.

* * * * *